US008591532B2

(12) United States Patent  (10) Patent No.: US 8,591,532 B2
Ortiz et al.  (45) Date of Patent: Nov. 26, 2013

(54) AUTOMATICALLY ADJUSTING BAND SYSTEM

(75) Inventors: Mark S. Ortiz, Milford, OH (US);
Daniel F. Dlugos, Jr., Middletown, OH (US); David N. Plescia, Cincinnati, OH (US); David C. Yates, West Chester, OH (US); Jason L. Harris, Mason, OH (US); Mark S. Zeiner, Mason, OH (US)

(73) Assignee: Ethicon Endo-Sugery, Inc., Cincinnati, OH (US)

( * ) Notice: Subject to any disclaimer, the term of this patent is extended or adjusted under 35 U.S.C. 154(b) by 1161 days.

(21) Appl. No.: 12/029,806

(22) Filed: Feb. 12, 2008

(65) Prior Publication Data
US 2009/0204132 A1  Aug. 13, 2009

(51) Int. Cl.
*A61B 17/08* (2006.01)
(52) U.S. Cl.
USPC ........................................................ 606/151
(58) Field of Classification Search
USPC ........................................................ 606/151
See application file for complete search history.

(56) References Cited

U.S. PATENT DOCUMENTS

| RE3,036 E | 7/1868 | Shunk |
| RE3,037 E | 7/1868 | Tucker |
| RE3,115 E | 9/1868 | Lewis |
| RE3,187 E | 11/1868 | Winchester |
| RE3,322 E | 3/1869 | Murch |
| 236,373 A | 1/1881 | Spilman |
| 322,388 A | 7/1885 | H.S. Lord |
| 400,401 A | 3/1889 | Gutzkow |
| D23,637 S | 9/1894 | Casad |
| D24,900 S | 11/1895 | Clemecet |
| D25,318 S | 3/1896 | Perky |
| D27,151 S | 6/1897 | Moulten |
| D29,715 S | 11/1898 | Wheeler |
| D29,745 S | 11/1898 | Bunker |
| D29,885 S | 12/1898 | Gillespi et al. |
| D30,690 S | 5/1899 | Schwedtmann |
| D30,966 S | 6/1899 | Howe |

(Continued)

FOREIGN PATENT DOCUMENTS

| CA | 1059035 | 7/1979 |
| CA | 1119469 | 3/1982 |

(Continued)

OTHER PUBLICATIONS

European Search Report, Application No. 08253986.7, Issued Mar. 30, 2009, 5 pages.

(Continued)

*Primary Examiner* — Corrine M McDermott
*Assistant Examiner* — Son Dang

(57) ABSTRACT

Devices and methods for forming a restriction in a patient are disclosed. In one exemplary embodiment, a restriction system is provided including an implantable restriction device, an implantable port in fluid communication with the implantable restriction device, and an implantable pump in fluid communication with the restriction device. In general, the implantable restriction device is adjustable and configured to form a restriction in a patient, and the implantable port is configured to receive fluid from a fluid source external to the patient. The implantable pump has a plurality of actuators configured to change shape upon the application of energy thereto such that sequential activation of the plurality of actuators is effective to create pumping action to move fluid through the pump.

16 Claims, 11 Drawing Sheets

(56) References Cited

U.S. PATENT DOCUMENTS

| | | |
|---|---|---|
| D31,230 S | 7/1899 | Hogan |
| 689,758 A | 12/1901 | Shaw |
| 724,913 A | 4/1903 | Montgomery |
| 899,477 A | 9/1908 | Williams |
| 926,197 A | 6/1909 | Kim |
| 953,875 A | 4/1910 | Waring |
| 991,192 A | 5/1911 | Batttenfeld |
| 1,087,988 A | 2/1914 | Sheldon |
| 1,210,701 A | 1/1917 | Ryden |
| 1,219,296 A | 3/1917 | Hahn |
| 1,224,355 A | 5/1917 | Brown |
| 1,263,914 A | 4/1918 | Martin |
| 1,310,290 A | 7/1919 | Piechowicz |
| 1,384,873 A | 7/1921 | Strickland |
| 1,421,507 A | 7/1922 | Lindberg |
| 1,551,525 A | 8/1925 | Hamer |
| 1,560,973 A | 11/1925 | J.J. Cheron |
| 1,620,633 A | 3/1927 | C.H. Colvin |
| 1,623,403 A | 4/1927 | Friel |
| 1,689,085 A | 10/1928 | Russell et al. |
| 1,764,071 A | 6/1930 | Foulke |
| 1,782,704 A | 11/1930 | Woodruff |
| 1,807,107 A | 5/1931 | Sternberch |
| 1,865,446 A | 7/1932 | Sears |
| 1,882,338 A | 10/1932 | Reed et al. |
| 1,924,781 A | 8/1933 | Gaiser |
| 2,027,875 A | 1/1936 | Odend'hal |
| 2,063,430 A | 12/1936 | Graser |
| 2,099,160 A | 11/1937 | Charch |
| 2,105,127 A | 1/1938 | Petrone |
| 2,106,192 A | 1/1938 | Saville |
| 2,143,429 A | 1/1939 | Auble |
| 2,166,603 A | 7/1939 | Menzer |
| 2,168,427 A | 8/1939 | McConkey |
| 2,174,525 A | 10/1939 | Padernal |
| 2,177,564 A | 10/1939 | Havill |
| 2,178,463 A | 10/1939 | Bahnson |
| 2,180,599 A | 11/1939 | Menasco |
| 2,203,460 A | 6/1940 | Fieber |
| 2,206,038 A | 7/1940 | Lang Ford |
| 2,216,374 A | 10/1940 | Martin |
| 2,223,699 A | 12/1940 | Norgren |
| 2,225,145 A | 12/1940 | Baumbach |
| 2,225,880 A | 12/1940 | Montelius |
| 2,261,060 A | 10/1941 | Giesler |
| 2,261,355 A | 11/1941 | Flynn |
| 2,295,539 A | 9/1942 | Beach |
| 2,303,108 A | 11/1942 | Blackburn |
| 2,303,502 A | 12/1942 | Rous |
| 2,318,819 A | 5/1943 | Verson |
| 2,327,407 A | 8/1943 | Edyvean |
| 2,327,615 A | 8/1943 | Ankarlo |
| 2,354,571 A | 7/1944 | Blain |
| 2,426,392 A | 8/1947 | Fennema |
| 2,426,817 A | 9/1947 | Charlton et al. |
| 2,440,260 A | 4/1948 | Gall |
| 2,442,573 A | 6/1948 | Stafford |
| 2,453,217 A | 11/1948 | Gregg et al. |
| 2,455,859 A | 12/1948 | Foley |
| 2,477,922 A | 8/1949 | Emery et al. |
| 2,478,876 A | 8/1949 | Nelson |
| 2,482,392 A | 9/1949 | Whitaker |
| 2,494,881 A | 1/1950 | Kost |
| 2,509,210 A | 5/1950 | Clark |
| 2,509,673 A | 5/1950 | Church |
| 2,511,765 A | 6/1950 | Bradbury |
| 2,520,056 A | 8/1950 | Pozun |
| 2,521,976 A | 9/1950 | Hays |
| 2,533,924 A | 12/1950 | Foley |
| 2,538,259 A | 1/1951 | Merriman |
| 2,581,479 A | 1/1952 | Grashman |
| 2,600,324 A | 6/1952 | Rappaport |
| 2,606,003 A | 8/1952 | McNeill |
| 2,615,940 A | 10/1952 | Williams |
| 2,632,447 A | 3/1953 | Dobes |
| 2,639,342 A | 5/1953 | Cope |
| 2,640,119 A | 5/1953 | Bradford, Jr. |
| 2,641,742 A | 6/1953 | Wolfe |
| 2,651,304 A | 9/1953 | Browner |
| 2,665,577 A | 1/1954 | Sanowskis |
| 2,673,999 A | 4/1954 | Shey |
| 2,676,609 A | 4/1954 | Pfarrer |
| 2,684,118 A | 7/1954 | Osmun |
| 2,689,611 A | 9/1954 | Martinson |
| 2,697,435 A | 12/1954 | Ray |
| 2,723,323 A | 11/1955 | Niemi |
| 2,734,992 A | 2/1956 | Elliot et al. |
| 2,740,007 A | 3/1956 | Amelang |
| 2,740,853 A | 4/1956 | Hatman, Jr. |
| 2,742,323 A | 4/1956 | Shey |
| 2,747,332 A | 5/1956 | Morehouse |
| 2,753,876 A | 7/1956 | Kurt |
| 2,756,883 A | 7/1956 | Schreck |
| 2,756,983 A | 7/1956 | Furcini |
| 2,761,603 A | 9/1956 | Fairchild |
| 2,773,312 A | 12/1956 | Peck |
| 2,783,728 A | 3/1957 | Hoffmann |
| 2,787,875 A | 4/1957 | Johnson |
| 2,793,379 A | 5/1957 | Moore |
| 2,795,460 A | 6/1957 | Bletcher |
| 2,804,514 A | 8/1957 | Peters |
| 2,822,113 A | 2/1958 | Joiner, Jr. |
| 2,831,478 A | 4/1958 | Uddenberg et al. |
| 2,864,393 A | 12/1958 | Drake |
| 2,865,541 A | 12/1958 | Hicks |
| 2,870,024 A | 1/1959 | Martin |
| 2,883,995 A | 4/1959 | Bialous et al. |
| 2,886,355 A | 5/1959 | Wurzel |
| 2,895,215 A | 7/1959 | Neher et al. |
| 2,899,493 A | 8/1959 | Levine |
| 2,902,861 A | 9/1959 | Frost et al. |
| 2,923,531 A | 2/1960 | Bauer et al. |
| 2,924,263 A | 2/1960 | Landis |
| 2,924,432 A | 2/1960 | Arps et al. |
| 2,930,170 A | 3/1960 | Holsman et al. |
| 2,938,592 A | 5/1960 | Charske et al. |
| 2,941,338 A | 6/1960 | Santschi |
| 2,943,682 A | 7/1960 | Ingram, Jr. et al. |
| 2,958,781 A | 11/1960 | Marchal et al. |
| 2,961,479 A | 11/1960 | Bertling |
| 2,976,355 A | 3/1961 | Levine |
| 2,976,686 A | 3/1961 | Stelzer |
| 2,977,876 A | 4/1961 | Meyers |
| 2,986,715 A | 5/1961 | Church et al. |
| 2,989,019 A | 6/1961 | Van Sciver, II |
| 3,010,692 A | 11/1961 | Jentoft |
| 3,013,234 A | 12/1961 | Bourns |
| 3,018,791 A | 1/1962 | Knox |
| 3,034,356 A | 5/1962 | Bieganski |
| 3,040,800 A | 6/1962 | Hartley |
| 3,054,618 A | 9/1962 | Abrams et al. |
| 3,060,262 A | 10/1962 | Hoer |
| 3,070,373 A | 12/1962 | Mathews et al. |
| 3,082,414 A | 3/1963 | Papaminas |
| 3,085,577 A | 4/1963 | Berman et al. |
| 3,096,410 A | 7/1963 | Anderson |
| 3,099,262 A | 7/1963 | Bigliano |
| 3,125,028 A | 3/1964 | Rohde |
| 3,126,029 A | 3/1964 | Englesson |
| 3,129,072 A | 4/1964 | Cook et al. |
| 3,135,914 A | 6/1964 | Callan et al. |
| 3,144,017 A | 8/1964 | Muth |
| 3,151,258 A | 9/1964 | Sonderegger et al. |
| 3,153,460 A | 10/1964 | Raskin |
| 3,161,051 A | 12/1964 | Perry, Jr. |
| 3,167,044 A | 1/1965 | Henrickson |
| 3,171,549 A | 3/1965 | Orloff |
| 3,172,700 A | 3/1965 | Haas |
| 3,173,269 A | 3/1965 | Imbertson |
| 3,182,494 A | 5/1965 | Beatty et al. |
| 3,187,181 A | 6/1965 | Keller |
| 3,187,745 A | 6/1965 | Baum et al. |
| 3,190,388 A | 6/1965 | Moser et al. |
| 3,205,547 A | 9/1965 | Riekse |

(56) References Cited

U.S. PATENT DOCUMENTS

| | | |
|---|---|---|
| 3,208,255 A | 9/1965 | Burk |
| 3,209,570 A | 10/1965 | Hills |
| 3,221,468 A | 12/1965 | Casey |
| 3,228,703 A | 1/1966 | Wilson |
| 3,229,684 A | 1/1966 | Nagumo et al. |
| 3,236,088 A | 2/1966 | Moller |
| 3,238,624 A | 3/1966 | McCabe |
| 3,240,510 A | 3/1966 | Spouge |
| 3,245,642 A | 4/1966 | Dicke |
| 3,255,568 A | 6/1966 | Martin et al. |
| 3,260,091 A | 7/1966 | Shaw, Jr. |
| 3,265,822 A | 8/1966 | Moulten |
| 3,266,487 A | 8/1966 | Watkins et al. |
| 3,273,447 A | 9/1966 | Frank |
| 3,283,352 A | 11/1966 | Hu |
| 3,290,919 A | 12/1966 | Malinak et al. |
| 3,292,493 A | 12/1966 | Franklin |
| 3,292,888 A | 12/1966 | Fischer |
| 3,294,988 A | 12/1966 | Packard |
| 3,299,603 A | 1/1967 | Shaw |
| 3,299,882 A | 1/1967 | Masino |
| 3,301,514 A | 1/1967 | Sugaya |
| 3,302,457 A | 2/1967 | Mayes |
| 3,306,384 A | 2/1967 | Ross |
| 3,313,314 A | 4/1967 | Burke et al. |
| 3,316,935 A | 5/1967 | Kaiser et al. |
| 3,320,750 A | 5/1967 | Haise et al. |
| 3,321,035 A | 5/1967 | Tarpley |
| 3,332,788 A | 7/1967 | Barnby |
| 3,334,510 A | 8/1967 | Hallesy |
| 3,339,401 A | 9/1967 | Peters |
| 3,340,868 A | 9/1967 | Darling |
| 3,347,162 A | 10/1967 | Braznell |
| 3,350,944 A | 11/1967 | De Michele |
| 3,353,364 A | 11/1967 | Blanding et al. |
| 3,353,481 A | 11/1967 | Antonucci |
| 3,356,334 A | 12/1967 | Scaramucci |
| 3,356,510 A | 12/1967 | Barnby |
| 3,357,218 A | 12/1967 | Mitchell |
| 3,357,461 A | 12/1967 | Friendship |
| 3,359,741 A | 12/1967 | Nelson |
| 3,361,300 A | 1/1968 | Kaplan |
| 3,364,929 A | 1/1968 | Ide et al. |
| 3,365,684 A | 1/1968 | Stemke |
| 3,378,456 A | 4/1968 | Roberts |
| 3,380,445 A | 4/1968 | Frasier |
| 3,380,649 A | 4/1968 | Roberts |
| 3,385,022 A | 5/1968 | Anderson |
| 3,389,355 A | 6/1968 | Schroeder, Jr. |
| 3,393,612 A | 7/1968 | Gorgens at al. |
| 3,396,561 A | 8/1968 | Day |
| 3,399,667 A | 9/1968 | Nishimoto at al. |
| 3,400,734 A | 9/1968 | Rosenberg |
| 3,403,237 A | 9/1968 | Wysong |
| 3,409,924 A | 11/1968 | Slama |
| 3,411,347 A | 11/1968 | Wirth at al. |
| 3,417,476 A | 12/1968 | Martens |
| 3,420,325 A | 1/1969 | McAlister et al. |
| 3,422,324 A | 1/1969 | Webb |
| 3,426,165 A | 2/1969 | Beaman |
| 3,438,391 A | 4/1969 | Yocum |
| 3,443,608 A | 5/1969 | Copping et al. |
| 3,445,335 A | 5/1969 | Gluntz |
| 3,447,281 A | 6/1969 | Bufford et al. |
| 3,450,153 A | 6/1969 | Hildebrandt et al. |
| 3,453,546 A | 7/1969 | Fryer |
| 3,453,848 A | 7/1969 | Williamson |
| 3,456,134 A | 7/1969 | Ko |
| 3,457,909 A | 7/1969 | Laird |
| 3,460,557 A | 8/1969 | Gallant |
| 3,463,338 A | 8/1969 | Schneider |
| 3,469,818 A | 9/1969 | Cowan |
| 3,470,725 A | 10/1969 | Brown et al. |
| 3,472,230 A | 10/1969 | Fogarty |
| 3,478,344 A | 11/1969 | Schwitzgebel et al. |
| 3,482,449 A | 12/1969 | Werner |
| 3,482,816 A | 12/1969 | Arnold |
| 3,487,959 A | 1/1970 | Pearne et al. |
| 3,491,842 A | 1/1970 | Delacour et al. |
| 3,492,638 A | 1/1970 | Lane |
| 3,502,829 A | 3/1970 | Reynolds |
| 3,503,116 A | 3/1970 | Strack |
| 3,504,664 A | 4/1970 | Haddad |
| 3,505,808 A | 4/1970 | Eschle |
| 3,509,754 A | 5/1970 | Massingill et al. |
| 3,512,517 A | 5/1970 | Kadish et al. |
| 3,514,919 A | 6/1970 | Ashton et al. |
| 3,516,220 A | 6/1970 | Buford et al. |
| 3,517,553 A | 6/1970 | Williams et al. |
| 3,527,226 A | 9/1970 | Hakin et al. |
| 3,529,908 A | 9/1970 | Smith |
| 3,530,449 A | 9/1970 | Anderson |
| 3,533,403 A | 10/1970 | Woodson |
| 3,534,728 A | 10/1970 | Barrows |
| 3,534,872 A | 10/1970 | Roth et al. |
| 3,535,914 A | 10/1970 | Veith at al. |
| 3,539,009 A | 11/1970 | Kudlaty |
| 3,543,744 A | 12/1970 | LePar |
| 3,545,275 A | 12/1970 | Harrison et al. |
| 3,550,583 A | 12/1970 | Chiku |
| 3,550,847 A | 12/1970 | Scott |
| 3,563,094 A | 2/1971 | Rieschel |
| 3,563,245 A | 2/1971 | McLean et al. |
| 3,566,083 A | 2/1971 | McMillin |
| 3,566,875 A | 3/1971 | Stoehr |
| 3,568,367 A | 3/1971 | Myers |
| 3,568,636 A | 3/1971 | Lockwood |
| 3,576,554 A | 4/1971 | Temps, Jr. et al. |
| 3,580,082 A | 5/1971 | Strack |
| 3,581,402 A | 6/1971 | London et al. |
| 3,583,387 A | 6/1971 | Garner et al. |
| 3,587,204 A | 6/1971 | George |
| 3,590,809 A | 7/1971 | London |
| 3,590,818 A | 7/1971 | Lemole |
| 3,590,992 A | 7/1971 | Soderstrom et al. |
| 3,592,183 A | 7/1971 | Watkins et al. |
| 3,594,519 A | 7/1971 | Schmidlin |
| 3,602,885 A | 8/1971 | Grajeda |
| 3,610,016 A | 10/1971 | Bultman |
| 3,610,851 A | 10/1971 | Krupski |
| 3,611,811 A | 10/1971 | Lissau |
| 3,614,926 A | 10/1971 | Brechtel |
| 3,614,955 A | 10/1971 | Mirowski et al. |
| 3,619,742 A | 11/1971 | Rud, Jr. |
| 3,623,371 A | 11/1971 | Jullien-Davin |
| 3,624,854 A | 12/1971 | Strong |
| 3,630,242 A | 12/1971 | Schieser et al. |
| 3,631,847 A | 1/1972 | Hobbs, II |
| 3,633,881 A | 1/1972 | Yurdin |
| 3,635,061 A | 1/1972 | Rydell et al. |
| 3,635,074 A | 1/1972 | Moos et al. |
| 3,638,496 A | 2/1972 | King |
| 3,644,883 A | 2/1972 | Borman et al. |
| 3,648,687 A | 3/1972 | Ramsey, III |
| 3,651,289 A | 3/1972 | Nagashima et al. |
| 3,651,405 A | 3/1972 | Whitney et al. |
| 3,653,671 A | 4/1972 | Shipes |
| 3,659,615 A | 5/1972 | Enger |
| 3,677,685 A | 7/1972 | Aoki et al. |
| 3,686,958 A | 8/1972 | Porter et al. |
| 3,688,568 A | 9/1972 | Karper et al. |
| 3,701,392 A | 10/1972 | Wirth et al. |
| 3,702,677 A | 11/1972 | Heffington |
| 3,703,099 A | 11/1972 | Rouse et al. |
| 3,712,138 A | 1/1973 | Alinari et al. |
| 3,713,124 A | 1/1973 | Durland et al. |
| 3,719,524 A | 3/1973 | Ripley et al. |
| 3,721,412 A | 3/1973 | Kindorf |
| 3,723,247 A | 3/1973 | Leine et al. |
| 3,724,000 A | 4/1973 | Eakman |
| 3,727,463 A | 4/1973 | Intraub |
| 3,727,616 A | 4/1973 | Lenzkes |
| 3,730,174 A | 5/1973 | Madison |
| 3,730,560 A | 5/1973 | Abildgaard et al. |

(56) References Cited

U.S. PATENT DOCUMENTS

| | | |
|---|---|---|
| 3,731,679 A | 5/1973 | Wilhelmson et al. |
| 3,731,681 A | 5/1973 | Blackshear et al. |
| 3,732,731 A | 5/1973 | Fussell, Jr. |
| 3,735,040 A | 5/1973 | Punt et al. |
| 3,736,930 A | 6/1973 | Georgi |
| 3,738,356 A | 6/1973 | Workman |
| 3,740,921 A | 6/1973 | Meyer et al. |
| 3,746,111 A | 7/1973 | Berthiaume et al. |
| 3,748,678 A | 7/1973 | Ballou |
| 3,749,098 A | 7/1973 | De Bennetot et al. |
| 3,749,422 A | 7/1973 | Abildgaard et al. |
| 3,749,423 A | 7/1973 | Abildgaard et al. |
| 3,750,194 A | 8/1973 | Summers |
| 3,757,770 A | 9/1973 | Brayshaw et al. |
| 3,759,095 A | 9/1973 | Short, Jr. et al. |
| 3,760,638 A | 9/1973 | Lawson et al. |
| 3,763,960 A | 10/1973 | John et al. |
| 3,765,142 A | 10/1973 | Lindquist et al. |
| 3,765,494 A | 10/1973 | Kielman, Jr. |
| 3,769,156 A | 10/1973 | Brecy et al. |
| 3,769,830 A | 11/1973 | Porter et al. |
| 3,774,243 A | 11/1973 | Ng et al. |
| 3,776,333 A | 12/1973 | Mathauser |
| 3,778,051 A | 12/1973 | Allen et al. |
| 3,780,578 A | 12/1973 | Sellman et al. |
| 3,781,902 A | 12/1973 | Shim et al. |
| 3,783,585 A | 1/1974 | Hoyland et al. |
| 3,789,667 A | 2/1974 | Porter et al. |
| 3,796,095 A | 3/1974 | Fussell, Jr. |
| 3,807,219 A | 4/1974 | Wallskog |
| 3,811,429 A | 5/1974 | Fletcher et al. |
| 3,815,722 A | 6/1974 | Sessoms |
| 3,818,765 A | 6/1974 | Eriksen et al. |
| 3,820,400 A | 6/1974 | Russo |
| 3,820,795 A | 6/1974 | Taylor |
| 3,823,610 A | 7/1974 | Fussell, Jr. |
| 3,825,065 A | 7/1974 | Lloyd et al. |
| 3,825,963 A | 7/1974 | Abildgaard et al. |
| 3,825,964 A | 7/1974 | Groswith, III et al. |
| 3,828,672 A | 8/1974 | Gazzola et al. |
| 3,828,766 A | 8/1974 | Krasnow |
| 3,831,588 A | 8/1974 | Rindner |
| 3,831,942 A | 8/1974 | Del Mar |
| 3,833,238 A | 9/1974 | Liard et al. |
| 3,834,167 A | 9/1974 | Tabor |
| 3,834,739 A | 9/1974 | Abildgaard et al. |
| 3,835,523 A | 9/1974 | Stansfield et al. |
| 3,839,708 A | 10/1974 | Bredesen et al. |
| 3,842,483 A | 10/1974 | Cramer |
| 3,842,668 A | 10/1974 | Lippke et al. |
| 3,845,664 A | 11/1974 | Perry, Jr. |
| 3,845,751 A | 11/1974 | Runstetler |
| 3,845,757 A | 11/1974 | Weyer |
| 3,847,434 A | 11/1974 | Weman et al. |
| 3,850,208 A | 11/1974 | Hamilton |
| 3,853,117 A | 12/1974 | Murr |
| 3,854,469 A | 12/1974 | Giori et al. |
| 3,855,902 A | 12/1974 | Kirst et al. |
| 3,857,399 A | 12/1974 | Zacouto et al. |
| 3,857,452 A | 12/1974 | Hartman |
| 3,857,745 A | 12/1974 | Grausch et al. |
| 3,858,581 A | 1/1975 | Kamen |
| 3,863,622 A | 2/1975 | Buuck |
| 3,863,933 A | 2/1975 | Tredway |
| 3,867,950 A | 2/1975 | Fischell |
| 3,868,008 A | 2/1975 | Brumbaugh |
| 3,868,679 A | 2/1975 | Arneson |
| 3,871,599 A | 3/1975 | Takada et al. |
| 3,872,285 A | 3/1975 | Shum et al. |
| 3,874,388 A | 4/1975 | King et al. |
| 3,876,980 A | 4/1975 | Haemmig et al. |
| 3,878,908 A | 4/1975 | Andersson et al. |
| 3,881,528 A | 5/1975 | Mackenzie |
| 3,893,111 A | 7/1975 | Cotter |
| 3,893,451 A | 7/1975 | Durand et al. |
| 3,895,681 A | 7/1975 | Griffin et al. |
| 3,899,862 A | 8/1975 | Muys et al. |
| 3,904,234 A | 9/1975 | Hill et al. |
| 3,908,334 A | 9/1975 | Rychiger et al. |
| 3,908,461 A | 9/1975 | Turpen |
| 3,908,721 A | 9/1975 | McGahey et al. |
| 3,910,087 A | 10/1975 | Jones |
| 3,912,168 A | 10/1975 | Mullins et al. |
| 3,912,304 A | 10/1975 | Abildgaard et al. |
| 3,918,286 A | 11/1975 | Whitehead |
| 3,918,291 A | 11/1975 | Pauly et al. |
| 3,920,965 A | 11/1975 | Sohrwardy et al. |
| 3,921,682 A | 11/1975 | McGahey et al. |
| 3,922,951 A | 12/1975 | Linsinger et al. |
| 3,923,060 A | 12/1975 | Ellinwood, Jr. |
| 3,924,635 A | 12/1975 | Hakim et al. |
| 3,928,980 A | 12/1975 | Ganzinotti et al. |
| 3,929,175 A | 12/1975 | Coone |
| 3,930,682 A | 1/1976 | Booth |
| 3,930,852 A | 1/1976 | Tanaka et al. |
| 3,936,028 A | 2/1976 | Norton et al. |
| 3,940,122 A | 2/1976 | Janzen et al. |
| 3,940,630 A | 2/1976 | Bergonz |
| 3,942,299 A | 3/1976 | Bory et al. |
| 3,942,382 A | 3/1976 | Hok et al. |
| 3,942,516 A | 3/1976 | Glynn et al. |
| 3,942,536 A | 3/1976 | Mirowski et al. |
| 3,943,915 A | 3/1976 | Severson |
| 3,945,704 A | 3/1976 | Kraus et al. |
| 3,946,613 A | 3/1976 | Silver |
| 3,946,615 A | 3/1976 | Hluchan |
| 3,946,724 A | 3/1976 | La Balme et al. |
| 3,948,141 A | 4/1976 | Shinjo et al. |
| 3,949,388 A | 4/1976 | Fuller |
| 3,953,289 A | 4/1976 | Costes et al. |
| 3,954,271 A | 5/1976 | Tredway, Sr. |
| 3,958,558 A | 5/1976 | Dunphy et al. |
| 3,961,425 A | 6/1976 | Swanson et al. |
| 3,961,646 A | 6/1976 | Schon et al. |
| 3,962,895 A | 6/1976 | Rydell et al. |
| 3,962,921 A | 6/1976 | Lips |
| 3,963,019 A | 6/1976 | Quandt |
| 3,964,485 A | 6/1976 | Neumeier |
| 3,964,770 A | 6/1976 | Abildgaard et al. |
| 3,967,737 A | 7/1976 | Peralta et al. |
| 3,968,473 A | 7/1976 | Patton et al. |
| 3,968,694 A | 7/1976 | Clark |
| 3,972,320 A | 8/1976 | Kalman |
| 3,973,753 A | 8/1976 | Wheeler |
| 3,973,858 A | 8/1976 | Poisson et al. |
| 3,974,655 A | 8/1976 | Halpern et al. |
| 3,974,865 A | 8/1976 | Fenton et al. |
| 3,977,391 A | 8/1976 | Fleischmann |
| 3,980,871 A | 9/1976 | Lindstrom et al. |
| 3,982,571 A | 9/1976 | Fenton et al. |
| 3,983,948 A | 10/1976 | Jeter |
| 3,985,133 A | 10/1976 | Jenkins et al. |
| 3,987,860 A | 10/1976 | Jabsen |
| 3,989,005 A | 11/1976 | Bowler, Jr. et al. |
| 3,991,749 A | 11/1976 | Zent |
| 3,992,948 A | 11/1976 | D'Antonio et al. |
| 3,993,149 A | 11/1976 | Harvey |
| 3,996,927 A | 12/1976 | Frank |
| 3,996,962 A | 12/1976 | Sutherland |
| 4,003,141 A | 1/1977 | Le Roy |
| 4,005,282 A | 1/1977 | Jennings |
| 4,005,593 A | 2/1977 | Goldberg |
| 4,006,735 A | 2/1977 | Hittman et al. |
| 4,009,375 A | 2/1977 | White et al. |
| 4,009,591 A | 3/1977 | Hester |
| 4,010,449 A | 3/1977 | Faggin et al. |
| 4,014,319 A | 3/1977 | Favre et al. |
| 4,014,321 A | 3/1977 | March |
| 4,016,764 A | 4/1977 | Rice |
| 4,017,329 A | 4/1977 | Larson |
| 4,018,134 A | 4/1977 | Linsinger et al. |
| 4,022,190 A | 5/1977 | Meyer |
| 4,024,864 A | 5/1977 | Davies et al. |
| 4,025,912 A | 5/1977 | Rice |

(56) References Cited

U.S. PATENT DOCUMENTS

| | | |
|---|---|---|
| 4,026,276 A | 5/1977 | Chubbuck |
| 4,027,661 A | 6/1977 | Lyon et al. |
| 4,031,899 A | 6/1977 | Renirie et al. |
| 4,036,775 A | 7/1977 | Trautvetter et al. |
| 4,039,069 A | 8/1977 | Kwan et al. |
| 4,041,954 A | 8/1977 | Ohara et al. |
| 4,042,504 A | 8/1977 | Drori et al. |
| 4,045,345 A | 8/1977 | Drori et al. |
| 4,047,851 A | 9/1977 | Bender |
| 4,048,494 A | 9/1977 | Liesting et al. |
| 4,048,879 A | 9/1977 | Cox |
| 4,049,004 A | 9/1977 | Walters |
| 4,051,338 A | 9/1977 | Harris, III |
| 4,052,991 A | 10/1977 | Zacouto et al. |
| 4,055,074 A | 10/1977 | Thimons et al. |
| 4,055,175 A | 10/1977 | Clemens et al. |
| 4,056,854 A | 11/1977 | Boretos et al. |
| 4,058,007 A | 11/1977 | Exner et al. |
| 4,062,351 A | 12/1977 | Hastwell et al. |
| 4,062,354 A | 12/1977 | Taylor et al. |
| 4,062,360 A | 12/1977 | Bentley |
| 4,063,439 A | 12/1977 | Besson et al. |
| 4,064,882 A | 12/1977 | Johnson et al. |
| 4,070,239 A | 1/1978 | Bevilacqua |
| 4,072,047 A | 2/1978 | Reismuller et al. |
| 4,073,292 A | 2/1978 | Edelman |
| 4,075,099 A | 2/1978 | Pelton et al. |
| 4,075,602 A | 2/1978 | Clothier |
| 4,077,072 A | 3/1978 | Dezura et al. |
| 4,077,394 A | 3/1978 | McCurdy |
| 4,077,405 A | 3/1978 | Haerten et al. |
| 4,077,882 A | 3/1978 | Gangemi |
| 4,078,620 A | 3/1978 | Westlake et al. |
| 4,080,653 A | 3/1978 | Barnes, Jr. et al. |
| 4,084,752 A | 4/1978 | Hagiwara et al. |
| 4,086,488 A | 4/1978 | Hill |
| 4,087,568 A | 5/1978 | Fay et al. |
| 4,088,417 A | 5/1978 | Kosmowski |
| 4,089,329 A | 5/1978 | Couvillon, Jr. et al. |
| 4,090,802 A | 5/1978 | Bilz et al. |
| 4,092,719 A | 5/1978 | Salmon et al. |
| 4,092,925 A | 6/1978 | Fromson |
| 4,096,866 A | 6/1978 | Fischell |
| 4,098,293 A | 7/1978 | Kramer et al. |
| 4,103,496 A | 8/1978 | Colamussi et al. |
| 4,106,370 A | 8/1978 | Kraus et al. |
| 4,107,689 A | 8/1978 | Jellinek |
| 4,107,995 A | 8/1978 | Ligman et al. |
| 4,108,148 A | 8/1978 | Cannon, III |
| 4,108,575 A | 8/1978 | Schal et al. |
| 4,109,148 A | 8/1978 | Jaulmes et al. |
| 4,109,518 A | 8/1978 | Dooley et al. |
| 4,109,644 A | 8/1978 | Kojima |
| 4,111,056 A | 9/1978 | Mastromatteo |
| 4,111,629 A | 9/1978 | Nussbaumer et al. |
| 4,114,424 A | 9/1978 | Johnson |
| 4,114,606 A | 9/1978 | Seylar |
| 4,120,097 A | 10/1978 | Jeter |
| 4,120,134 A | 10/1978 | Scholle |
| 4,121,635 A | 10/1978 | Hansel |
| 4,123,310 A | 10/1978 | Varon et al. |
| 4,124,023 A | 11/1978 | Fleischmann et al. |
| 4,127,110 A | 11/1978 | Bullara |
| 4,130,169 A | 12/1978 | Denison |
| 4,131,596 A | 12/1978 | Allen |
| 4,133,355 A | 1/1979 | Mayer |
| 4,133,367 A | 1/1979 | Abell |
| 4,140,131 A | 2/1979 | Dutcher et al. |
| 4,141,348 A | 2/1979 | Hittman |
| 4,141,349 A | 2/1979 | Ory et al. |
| 4,143,661 A | 3/1979 | LaForge et al. |
| 4,146,029 A | 3/1979 | Ellinwood, Jr. |
| 4,147,161 A | 4/1979 | Ikebe et al. |
| 4,148,096 A | 4/1979 | Haas et al. |
| 4,149,423 A | 4/1979 | Frosch et al. |
| 4,151,823 A | 5/1979 | Grosse et al. |
| 4,153,085 A | 5/1979 | Adams |
| 4,156,422 A | 5/1979 | Hildebrandt et al. |
| 4,160,448 A | 7/1979 | Jackson |
| 4,160,971 A | 7/1979 | Jones et al. |
| 4,166,469 A | 9/1979 | Littleford |
| 4,167,304 A | 9/1979 | Gelbke |
| 4,167,952 A | 9/1979 | Reinicke |
| 4,168,567 A | 9/1979 | Leguy et al. |
| 4,170,280 A | 10/1979 | Schwarz |
| 4,171,218 A | 10/1979 | Hoshino et al. |
| 4,183,124 A | 1/1980 | Hoffman |
| 4,183,247 A | 1/1980 | Allen et al. |
| 4,185,641 A | 1/1980 | Minior et al. |
| 4,186,287 A | 1/1980 | Scott |
| 4,186,749 A | 2/1980 | Fryer |
| 4,186,751 A | 2/1980 | Fleischmann |
| 4,190,057 A | 2/1980 | Hill et al. |
| 4,191,004 A | 3/1980 | Gmuer et al. |
| 4,191,187 A | 3/1980 | Wright et al. |
| 4,192,192 A | 3/1980 | Schnell |
| 4,193,397 A | 3/1980 | Tucker et al. |
| 4,204,547 A | 5/1980 | Allocca |
| 4,206,755 A | 6/1980 | Klein et al. |
| 4,206,761 A | 6/1980 | Cosman |
| 4,206,762 A | 6/1980 | Cosman |
| 4,207,903 A | 6/1980 | O'Neill |
| 4,212,074 A | 7/1980 | Kuno et al. |
| 4,217,221 A | 8/1980 | Masso |
| 4,217,588 A | 8/1980 | Freeny, Jr. |
| 4,220,189 A | 9/1980 | Marquez |
| 4,221,219 A | 9/1980 | Tucker |
| 4,221,523 A | 9/1980 | Eberle |
| 4,222,377 A | 9/1980 | Burton |
| 4,223,837 A | 9/1980 | Gubbiotti et al. |
| 4,226,124 A | 10/1980 | Kersten et al. |
| 4,226,229 A | 10/1980 | Eckhart et al. |
| 4,227,533 A | 10/1980 | Godfrey |
| 4,231,376 A | 11/1980 | Lyon et al. |
| 4,232,682 A | 11/1980 | Veth |
| 4,237,900 A | 12/1980 | Schulman et al. |
| 4,241,247 A | 12/1980 | Byrne et al. |
| 4,241,870 A | 12/1980 | Marcus |
| 4,245,593 A | 1/1981 | Stein |
| 4,246,877 A | 1/1981 | Kennedy |
| 4,247,850 A | 1/1981 | Marcus |
| 4,248,238 A | 2/1981 | Joseph et al. |
| 4,248,241 A | 2/1981 | Tacchi |
| 4,256,094 A | 3/1981 | Kapp et al. |
| 4,256,118 A | 3/1981 | Nagel et al. |
| 4,262,343 A | 4/1981 | Claycomb |
| 4,262,632 A | 4/1981 | Hanton et al. |
| 4,265,241 A | 5/1981 | Portner et al. |
| 4,265,252 A | 5/1981 | Chubbuck et al. |
| 4,271,018 A | 6/1981 | Drori et al. |
| 4,273,070 A | 6/1981 | Hoefelmayr et al. |
| 4,274,444 A | 6/1981 | Ruyak |
| 4,275,600 A | 6/1981 | Turner et al. |
| 4,275,913 A | 6/1981 | Marcus |
| 4,278,540 A | 7/1981 | Drori et al. |
| 4,280,036 A | 7/1981 | Fukatsu et al. |
| 4,280,775 A | 7/1981 | Wood |
| 4,281,666 A | 8/1981 | Cosman |
| 4,281,667 A | 8/1981 | Cosman |
| 4,284,073 A | 8/1981 | Krause et al. |
| 4,285,770 A | 8/1981 | Chi et al. |
| 4,291,699 A | 9/1981 | Geddes et al. |
| 4,295,963 A | 10/1981 | Drori et al. |
| 4,297,927 A | 11/1981 | Kuroda et al. |
| 4,303,075 A | 12/1981 | Heilman et al. |
| 4,305,402 A | 12/1981 | Katims |
| 4,312,374 A | 1/1982 | Drori et al. |
| 4,314,480 A | 2/1982 | Becker |
| 4,316,693 A | 2/1982 | Baxter et al. |
| 4,325,387 A | 4/1982 | Helfer |
| 4,327,804 A | 5/1982 | Reed |
| 4,328,654 A | 5/1982 | Van Ginkel et al. |
| 4,332,254 A | 6/1982 | Lundquist |
| 4,339,831 A | 7/1982 | Johnson |

(56) References Cited

U.S. PATENT DOCUMENTS

| | | |
|---|---|---|
| 4,342,218 A | 8/1982 | Fox |
| 4,342,308 A | 8/1982 | Trick |
| 4,346,604 A | 8/1982 | Snook et al. |
| 4,347,851 A | 9/1982 | Jundanian |
| 4,350,647 A | 9/1982 | de la Cruz |
| 4,350,970 A | 9/1982 | von Tomkewitsch et al. |
| 4,351,037 A | 9/1982 | Scherbatskoy |
| 4,351,116 A | 9/1982 | Scott, Jr. |
| 4,356,486 A | 10/1982 | Mount |
| 4,360,010 A | 11/1982 | Finney |
| 4,360,277 A | 11/1982 | Daniel et al. |
| 4,361,153 A | 11/1982 | Slocum et al. |
| 4,363,236 A | 12/1982 | Meyers |
| 4,364,276 A | 12/1982 | Shimazoe et al. |
| 4,365,425 A | 12/1982 | Gotchel |
| 4,368,937 A | 1/1983 | Palombo et al. |
| 4,369,013 A | 1/1983 | Abildgaard et al. |
| 4,373,527 A | 2/1983 | Fischell |
| 4,376,523 A | 3/1983 | Goyen et al. |
| 4,378,809 A | 4/1983 | Cosman |
| 4,380,427 A | 4/1983 | Hehl et al. |
| 4,385,636 A | 5/1983 | Cosman |
| 4,386,422 A | 5/1983 | Mumby et al. |
| 4,387,907 A | 6/1983 | Hiestand et al. |
| 4,392,368 A | 7/1983 | Folkesson et al. |
| 4,393,899 A | 7/1983 | Tsuji et al. |
| 4,393,951 A | 7/1983 | Horst-Rudolf et al. |
| 4,395,232 A | 7/1983 | Koch |
| 4,395,258 A | 7/1983 | Wang et al. |
| 4,395,916 A | 8/1983 | Martin |
| 4,398,983 A | 8/1983 | Suzuki et al. |
| 4,399,705 A | 8/1983 | Weiger et al. |
| 4,399,707 A | 8/1983 | Wamstad |
| 4,399,809 A | 8/1983 | Baro et al. |
| 4,399,821 A | 8/1983 | Bowers |
| 4,403,984 A | 9/1983 | Ash et al. |
| 4,404,968 A | 9/1983 | Evans, Sr. |
| 4,404,974 A | 9/1983 | Titus |
| 4,405,318 A | 9/1983 | Whitney et al. |
| 4,407,125 A | 10/1983 | Parsons et al. |
| 4,407,271 A | 10/1983 | Schiff |
| 4,407,296 A | 10/1983 | Anderson |
| 4,407,326 A | 10/1983 | Wilhelm |
| 4,408,597 A | 10/1983 | Tenney, Jr. |
| 4,408,615 A | 10/1983 | Grossman |
| 4,415,071 A | 11/1983 | Butler et al. |
| 4,416,282 A | 11/1983 | Saulson et al. |
| 4,418,899 A | 12/1983 | Zimmermann et al. |
| 4,419,393 A | 12/1983 | Hanson et al. |
| 4,421,505 A | 12/1983 | Schwartz |
| 4,424,720 A | 1/1984 | Bucchianeri |
| 4,428,228 A | 1/1984 | Banzhaf et al. |
| 4,428,365 A | 1/1984 | Hakky et al. |
| 4,430,899 A | 2/1984 | Wessel et al. |
| 4,431,009 A | 2/1984 | Marino, Jr. et al. |
| 4,431,365 A | 2/1984 | Sturtz, Jr. |
| 4,432,363 A | 2/1984 | Kakegawa et al. |
| 4,435,173 A | 3/1984 | Siposs et al. |
| 4,439,186 A | 3/1984 | Kuhl et al. |
| 4,441,491 A | 4/1984 | Evans, Sr. |
| 4,441,501 A | 4/1984 | Parent |
| 4,444,194 A | 4/1984 | Burcham |
| 4,444,498 A | 4/1984 | Heinemann |
| 4,445,385 A | 5/1984 | Endo |
| 4,446,711 A | 5/1984 | Valente |
| 4,447,224 A | 5/1984 | DeCant, Jr. et al. |
| 4,449,493 A | 5/1984 | Kopec et al. |
| 4,450,811 A | 5/1984 | Ichikawa et al. |
| 4,451,033 A | 5/1984 | Nestegard |
| 4,453,537 A | 6/1984 | Spitzer |
| 4,453,578 A | 6/1984 | Wilder |
| 4,460,835 A | 7/1984 | Masuoka et al. |
| 4,464,170 A | 8/1984 | Clemens et al. |
| 4,465,015 A | 8/1984 | Osta et al. |
| 4,465,474 A | 8/1984 | Mardorf et al. |
| 4,466,290 A | 8/1984 | Frick |
| 4,468,172 A | 8/1984 | Dixon et al. |
| 4,468,762 A | 8/1984 | Jurgens et al. |
| 4,469,365 A | 9/1984 | Marcus et al. |
| 4,471,182 A | 9/1984 | Wielgos et al. |
| 4,471,786 A | 9/1984 | Inagaki et al. |
| 4,473,067 A | 9/1984 | Schiff |
| 4,473,078 A | 9/1984 | Angel |
| 4,476,721 A | 10/1984 | Hochreuther et al. |
| 4,478,213 A | 10/1984 | Redding |
| 4,478,538 A | 10/1984 | Kakino et al. |
| 4,483,196 A | 11/1984 | Kurtz et al. |
| 4,484,135 A | 11/1984 | Ishihara et al. |
| 4,485,813 A | 12/1984 | Anderson et al. |
| 4,489,916 A | 12/1984 | Stevens |
| 4,492,632 A | 1/1985 | Mattson |
| 4,494,411 A | 1/1985 | Koschke et al. |
| 4,494,950 A | 1/1985 | Fischell |
| 4,497,176 A | 2/1985 | Rubin et al. |
| 4,497,201 A | 2/1985 | Allen et al. |
| 4,499,394 A | 2/1985 | Koal |
| 4,499,691 A | 2/1985 | Karazim et al. |
| 4,499,750 A | 2/1985 | Gerber et al. |
| 4,503,678 A | 3/1985 | Wimbush et al. |
| 4,511,974 A | 4/1985 | Nakane et al. |
| 4,513,295 A | 4/1985 | Jones et al. |
| 4,515,004 A | 5/1985 | Jaenson |
| 4,515,750 A | 5/1985 | Pardini et al. |
| 4,516,866 A | 5/1985 | Yamauchi et al. |
| 4,518,637 A | 5/1985 | Takeda et al. |
| 4,519,401 A | 5/1985 | Ko et al. |
| 4,520,443 A | 5/1985 | Yuki et al. |
| 4,522,213 A | 6/1985 | Wallroth et al. |
| 4,527,568 A | 7/1985 | Rickards et al. |
| 4,529,401 A | 7/1985 | Leslie et al. |
| 4,531,526 A | 7/1985 | Genest |
| 4,531,936 A | 7/1985 | Gordon |
| 4,536,000 A | 8/1985 | Rohm et al. |
| 4,537,005 A | 8/1985 | Hoyland et al. |
| 4,537,129 A | 8/1985 | Heinemann et al. |
| 4,538,616 A | 9/1985 | Rogoff |
| 4,540,404 A | 9/1985 | Wolvek |
| 4,542,461 A | 9/1985 | Eldridge et al. |
| 4,544,369 A | 10/1985 | Skakoon et al. |
| 4,545,185 A | 10/1985 | Chikatani et al. |
| 4,546,524 A | 10/1985 | Kreft |
| 4,548,209 A | 10/1985 | Wielders et al. |
| 4,552,150 A | 11/1985 | Zacouto et al. |
| 4,553,226 A | 11/1985 | Scherbatskoy |
| 4,556,063 A | 12/1985 | Thompson et al. |
| 4,557,269 A | 12/1985 | Reynolds et al. |
| 4,557,332 A | 12/1985 | Denison et al. |
| 4,559,815 A | 12/1985 | Needham et al. |
| 4,560,979 A | 12/1985 | Rosskopf et al. |
| 4,561,442 A | 12/1985 | Vollmann et al. |
| 4,562,751 A | 1/1986 | Nason et al. |
| 4,563,175 A | 1/1986 | LaFond |
| 4,565,116 A | 1/1986 | Hehl et al. |
| 4,566,456 A | 1/1986 | Koning et al. |
| 4,569,623 A | 2/1986 | Goldmann |
| 4,570,351 A | 2/1986 | Szanto et al. |
| 4,571,161 A | 2/1986 | Leblanc et al. |
| 4,571,995 A | 2/1986 | Timme |
| 4,573,835 A | 3/1986 | Eckardt et al. |
| 4,574,792 A | 3/1986 | Trick |
| 4,576,181 A | 3/1986 | Wallace et al. |
| 4,576,183 A | 3/1986 | Plicchi et al. |
| 4,577,512 A | 3/1986 | Lowenheck et al. |
| 4,581,018 A | 4/1986 | Jassawalla et al. |
| 4,581,915 A | 4/1986 | Haulsee et al. |
| 4,587,840 A | 5/1986 | Dobler et al. |
| 4,589,805 A | 5/1986 | Duffner et al. |
| 4,592,339 A | 6/1986 | Kuzmak et al. |
| 4,592,340 A | 6/1986 | Boyles |
| 4,593,703 A | 6/1986 | Cosman |
| 4,595,228 A | 6/1986 | Chu |
| 4,596,563 A | 6/1986 | Pande |
| 4,599,943 A | 7/1986 | Kobler et al. |
| 4,600,855 A | 7/1986 | Strachan et al. |

(56) References Cited

U.S. PATENT DOCUMENTS

| | | |
|---|---|---|
| 4,602,541 A | 7/1986 | Benzinger et al. |
| 4,604,089 A | 8/1986 | Santangelo et al. |
| 4,605,354 A | 8/1986 | Daly |
| 4,606,419 A | 8/1986 | Perini |
| 4,606,478 A | 8/1986 | Hack et al. |
| 4,610,256 A | 9/1986 | Wallace |
| 4,614,137 A | 9/1986 | Jones |
| 4,617,016 A | 10/1986 | Blomberg et al. |
| 4,618,861 A | 10/1986 | Gettens et al. |
| 4,620,807 A | 11/1986 | Polit |
| 4,621,331 A | 11/1986 | Iwata et al. |
| 4,622,871 A | 11/1986 | Van Sickle et al. |
| 4,626,462 A | 12/1986 | Kober et al. |
| 4,633,304 A | 12/1986 | Nagasaki et al. |
| 4,633,878 A | 1/1987 | Bombardieri et al. |
| 4,635,182 A | 1/1987 | Hintz |
| 4,637,736 A | 1/1987 | Andeen et al. |
| 4,638,665 A | 1/1987 | Benson et al. |
| 4,644,246 A | 2/1987 | Knapen et al. |
| 4,646,553 A | 3/1987 | Tufte et al. |
| 4,648,363 A | 3/1987 | Kronich |
| 4,648,406 A | 3/1987 | Miller |
| 4,658,358 A | 4/1987 | Leach et al. |
| 4,658,760 A | 4/1987 | Zebuhr |
| 4,660,568 A | 4/1987 | Cosman |
| 4,665,511 A | 5/1987 | Rodney et al. |
| 4,665,896 A | 5/1987 | LaForge et al. |
| 4,669,484 A | 6/1987 | Masters |
| 4,672,974 A | 6/1987 | Lee |
| 4,674,457 A | 6/1987 | Berger et al. |
| 4,674,546 A | 6/1987 | Fournier et al. |
| 4,678,408 A | 7/1987 | Nason et al. |
| 4,681,559 A | 7/1987 | Hooven |
| 4,683,850 A | 8/1987 | Bauder et al. |
| 4,685,463 A | 8/1987 | Williams |
| 4,685,469 A | 8/1987 | Keller et al. |
| 4,685,903 A | 8/1987 | Cable et al. |
| 4,686,987 A | 8/1987 | Salo et al. |
| 4,687,530 A | 8/1987 | Berscheid et al. |
| 4,689,979 A | 9/1987 | Otsuka et al. |
| 4,691,694 A | 9/1987 | Boyd et al. |
| 4,691,710 A | 9/1987 | Dickens et al. |
| 4,693,253 A | 9/1987 | Adams |
| 4,695,237 A | 9/1987 | Inaba et al. |
| 4,696,189 A | 9/1987 | Hochreuther et al. |
| 4,697,574 A | 10/1987 | Karcher et al. |
| 4,698,038 A | 10/1987 | Key et al. |
| 4,700,497 A | 10/1987 | Sato et al. |
| 4,700,610 A | 10/1987 | Bauer et al. |
| 4,701,143 A | 10/1987 | Key et al. |
| 4,703,756 A | 11/1987 | Gough et al. |
| 4,705,507 A | 11/1987 | Boyles |
| 4,706,948 A | 11/1987 | Kroecher et al. |
| 4,712,562 A | 12/1987 | Ohayon et al. |
| 4,718,425 A | 1/1988 | Tanaka et al. |
| 4,722,348 A | 2/1988 | Ligtenberg et al. |
| 4,724,806 A | 2/1988 | Hartwig et al. |
| 4,724,830 A | 2/1988 | Fischell |
| 4,725,826 A | 2/1988 | Hunter |
| 4,728,479 A | 3/1988 | Merkovsky |
| 4,729,517 A | 3/1988 | Krokor et al. |
| 4,730,188 A | 3/1988 | Milheiser |
| 4,730,420 A | 3/1988 | Stratmann et al. |
| 4,730,619 A | 3/1988 | Koning et al. |
| 4,731,058 A | 3/1988 | Doan |
| 4,735,205 A | 4/1988 | Chachques et al. |
| 4,738,267 A | 4/1988 | Lazorthes et al. |
| 4,738,268 A | 4/1988 | Kipnis |
| 4,741,345 A | 5/1988 | Matthews et al. |
| 4,741,732 A | 5/1988 | Crankshaw et al. |
| 4,743,129 A | 5/1988 | Keryhuel et al. |
| 4,745,541 A | 5/1988 | Vaniglia et al. |
| 4,746,830 A | 5/1988 | Holland |
| 4,750,495 A | 6/1988 | Moore et al. |
| 4,752,115 A | 6/1988 | Murray, Jr. et al. |
| 4,752,658 A | 6/1988 | Mack |
| 4,757,463 A | 7/1988 | Ballou et al. |
| 4,759,386 A | 7/1988 | Grouw, III |
| 4,763,649 A | 8/1988 | Merrick |
| 4,765,001 A | 8/1988 | Smith |
| 4,767,406 A | 8/1988 | Wadham et al. |
| 4,769,001 A | 9/1988 | Prince |
| 4,772,896 A | 9/1988 | Nakatsu et al. |
| 4,773,401 A | 9/1988 | Citak et al. |
| 4,774,950 A | 10/1988 | Cohen |
| 4,774,955 A | 10/1988 | Jones |
| 4,777,953 A | 10/1988 | Ash et al. |
| 4,779,626 A | 10/1988 | Peel et al. |
| 4,781,192 A | 11/1988 | Demer |
| 4,782,826 A | 11/1988 | Fogarty |
| 4,783,106 A | 11/1988 | Nutter |
| 4,788,847 A | 12/1988 | Sterghos |
| 4,791,318 A | 12/1988 | Lewis et al. |
| 4,794,803 A | 1/1989 | Osterhout et al. |
| 4,796,641 A | 1/1989 | Mills et al. |
| 4,798,211 A | 1/1989 | Goor et al. |
| 4,798,227 A | 1/1989 | Goodwin |
| 4,799,491 A | 1/1989 | Eckerle |
| 4,799,625 A | 1/1989 | Weaver, Jr. et al. |
| 4,802,488 A | 2/1989 | Eckerle |
| 4,803,987 A | 2/1989 | Calfee et al. |
| 4,804,368 A | 2/1989 | Skakoon et al. |
| 4,807,321 A | 2/1989 | Grasselli et al. |
| 4,808,167 A | 2/1989 | Mann et al. |
| 4,812,823 A | 3/1989 | Dickerson |
| 4,819,656 A | 4/1989 | Spector |
| 4,820,265 A | 4/1989 | DeSatnick et al. |
| 4,820,953 A | 4/1989 | Saubolle et al. |
| 4,821,167 A | 4/1989 | Wiebe |
| 4,821,723 A | 4/1989 | Baker, Jr. et al. |
| 4,823,779 A | 4/1989 | Daly et al. |
| 4,830,006 A | 5/1989 | Haluska et al. |
| 4,832,034 A | 5/1989 | Pizziconi et al. |
| 4,833,384 A | 5/1989 | Munro et al. |
| 4,834,731 A | 5/1989 | Nowak et al. |
| 4,838,857 A | 6/1989 | Strowe et al. |
| 4,840,068 A | 6/1989 | Mayhew, Jr. |
| 4,840,350 A | 6/1989 | Cook et al. |
| 4,844,002 A | 7/1989 | Yasui et al. |
| 4,846,153 A | 7/1989 | Berci |
| 4,846,191 A | 7/1989 | Brockway et al. |
| 4,846,664 A | 7/1989 | Hehl et al. |
| 4,854,328 A | 8/1989 | Pollack |
| 4,863,470 A | 9/1989 | Carter |
| 4,865,587 A | 9/1989 | Walling |
| 4,867,160 A | 9/1989 | Schaldach et al. |
| 4,867,498 A | 9/1989 | Delphia et al. |
| 4,867,618 A | 9/1989 | Brohammer |
| 4,869,252 A | 9/1989 | Gilli |
| 4,870,258 A | 9/1989 | Mochizuki et al. |
| 4,871,351 A | 10/1989 | Feingold et al. |
| 4,872,483 A | 10/1989 | Shah |
| 4,872,869 A | 10/1989 | Johns |
| 4,873,677 A | 10/1989 | Sakamoto et al. |
| 4,875,483 A | 10/1989 | Vollmann et al. |
| 4,880,004 A | 11/1989 | Baker, Jr. et al. |
| 4,882,678 A | 11/1989 | Hollis et al. |
| 4,886,392 A | 12/1989 | Iio et al. |
| 4,895,151 A | 1/1990 | Grevis et al. |
| 4,896,594 A | 1/1990 | Baur et al. |
| 4,898,158 A | 2/1990 | Daly et al. |
| 4,898,578 A | 2/1990 | Rubalcaba, Jr. |
| 4,899,751 A | 2/1990 | Cohen |
| 4,899,752 A | 2/1990 | Cohen |
| 4,902,277 A | 2/1990 | Mathies et al. |
| 4,903,701 A | 2/1990 | Moore et al. |
| 4,909,678 A | 3/1990 | Kakimoto et al. |
| 4,913,147 A | 4/1990 | Fahlstrom et al. |
| 4,919,143 A | 4/1990 | Ayers |
| 4,924,872 A | 5/1990 | Frank |
| 4,926,903 A | 5/1990 | Kawai et al. |
| 4,932,406 A | 6/1990 | Berkovits |
| 4,934,369 A | 6/1990 | Maxwell |
| 4,936,304 A | 6/1990 | Kresh et al. |

(56) References Cited

U.S. PATENT DOCUMENTS

| | | |
|---|---|---|
| 4,940,037 A | 7/1990 | Eckert et al. |
| 4,941,718 A | 7/1990 | Alexander, III et al. |
| 4,942,004 A | 7/1990 | Catanzaro |
| 4,944,050 A | 7/1990 | Shames et al. |
| 4,944,298 A | 7/1990 | Sholder |
| 4,944,307 A | 7/1990 | Hon et al. |
| 4,945,761 A | 8/1990 | Lessi et al. |
| 4,949,724 A | 8/1990 | Mahutte et al. |
| 4,952,205 A | 8/1990 | Mauerer et al. |
| 4,952,928 A | 8/1990 | Carroll et al. |
| 4,953,563 A | 9/1990 | Kaiser et al. |
| 4,954,677 A | 9/1990 | Alberter et al. |
| 4,958,630 A | 9/1990 | Rosenbluth et al. |
| 4,958,645 A | 9/1990 | Cadell et al. |
| 4,960,424 A | 10/1990 | Grooters |
| 4,960,966 A | 10/1990 | Evans et al. |
| 4,967,585 A | 11/1990 | Grimaldo |
| 4,967,761 A | 11/1990 | Nathanielsz |
| 4,970,823 A | 11/1990 | Chen et al. |
| 4,971,251 A | 11/1990 | Dobrick et al. |
| 4,977,896 A | 12/1990 | Robinson et al. |
| 4,978,335 A | 12/1990 | Arthur, III |
| 4,978,338 A | 12/1990 | Melsky et al. |
| 4,979,730 A | 12/1990 | Holbrook et al. |
| 4,980,671 A | 12/1990 | McCurdy |
| 4,981,141 A | 1/1991 | Segalowitz |
| 4,981,173 A | 1/1991 | Perkins et al. |
| 4,981,426 A | 1/1991 | Aoki et al. |
| 4,987,897 A | 1/1991 | Funke et al. |
| 4,988,337 A | 1/1991 | Ito et al. |
| 4,992,794 A | 2/1991 | Brouwers et al. |
| 4,997,556 A | 3/1991 | Yano et al. |
| 5,001,528 A | 3/1991 | Bahraman |
| 5,003,807 A | 4/1991 | Terrell et al. |
| 5,003,975 A | 4/1991 | Hafelfinger et al. |
| 5,003,976 A | 4/1991 | Alt et al. |
| 5,004,472 A | 4/1991 | Wallace |
| 5,004,873 A | 4/1991 | Schnut |
| 5,005,574 A | 4/1991 | Fearnot et al. |
| 5,005,586 A | 4/1991 | Lahr |
| 5,006,844 A | 4/1991 | Ohta et al. |
| 5,007,401 A | 4/1991 | Grohn et al. |
| 5,007,430 A | 4/1991 | Dardik |
| 5,007,919 A | 4/1991 | Silva et al. |
| 5,009,662 A | 4/1991 | Wallace et al. |
| 5,010,893 A | 4/1991 | Sholder |
| 5,012,286 A | 4/1991 | Kawano et al. |
| 5,012,810 A | 5/1991 | Strand et al. |
| 5,013,292 A | 5/1991 | Lemay et al. |
| 5,014,040 A | 5/1991 | Weaver et al. |
| 5,019,032 A | 5/1991 | Robertson |
| 5,019,041 A | 5/1991 | Robinson et al. |
| 5,020,845 A | 6/1991 | Falcoff et al. |
| 5,021,046 A | 6/1991 | Wallace |
| 5,022,395 A | 6/1991 | Russie |
| 5,024,965 A | 6/1991 | Chang et al. |
| 5,026,180 A | 6/1991 | Tajima et al. |
| 5,026,360 A | 6/1991 | Johnsen et al. |
| 5,028,918 A | 7/1991 | Giles et al. |
| 5,032,822 A | 7/1991 | Sweet |
| 5,036,869 A | 8/1991 | Inahara et al. |
| 5,038,800 A | 8/1991 | Oba et al. |
| 5,041,086 A | 8/1991 | Koenig et al. |
| 5,041,826 A | 8/1991 | Milheiser |
| 5,042,503 A | 8/1991 | Torok et al. |
| 5,044,770 A | 9/1991 | Haghkar |
| 5,046,661 A | 9/1991 | Kimura et al. |
| 5,048,060 A | 9/1991 | Arai et al. |
| 5,050,922 A | 9/1991 | Falcoff |
| 5,052,910 A | 10/1991 | Hehl et al. |
| 5,053,008 A | 10/1991 | Bajaj |
| 5,057,078 A | 10/1991 | Foote et al. |
| 5,058,583 A | 10/1991 | Geddes et al. |
| 5,061,239 A | 10/1991 | Shiels |
| 5,062,052 A | 10/1991 | Sparer et al. |
| 5,062,053 A | 10/1991 | Shirai et al. |
| 5,062,559 A | 11/1991 | Falcoff |
| 5,064,974 A | 11/1991 | Vigneau et al. |
| 5,067,960 A | 11/1991 | Grandjean et al. |
| 5,068,779 A | 11/1991 | Sullivan et al. |
| 5,069,680 A | 12/1991 | Grandjean et al. |
| 5,077,102 A | 12/1991 | Chong |
| 5,077,870 A | 1/1992 | Melbye et al. |
| 5,078,139 A | 1/1992 | Strand et al. |
| 5,082,006 A | 1/1992 | Jonasson et al. |
| 5,083,563 A | 1/1992 | Collins et al. |
| 5,084,699 A | 1/1992 | DeMichele |
| 5,085,224 A | 2/1992 | Galen et al. |
| 5,085,258 A | 2/1992 | Fink, Jr. et al. |
| 5,089,673 A | 2/1992 | Strzodka et al. |
| 5,089,979 A | 2/1992 | McEachern et al. |
| 5,095,309 A | 3/1992 | Troyk et al. |
| 5,096,271 A | 3/1992 | Portman |
| 5,097,831 A | 3/1992 | Lekholm |
| 5,098,384 A | 3/1992 | Abrams |
| 5,103,832 A | 4/1992 | Jackson |
| 5,105,810 A | 4/1992 | Collins et al. |
| 5,107,850 A | 4/1992 | Olive |
| 5,112,344 A | 5/1992 | Petros et al. |
| 5,113,859 A | 5/1992 | Funke et al. |
| 5,113,869 A | 5/1992 | Nappholz et al. |
| 5,115,676 A | 5/1992 | Lee |
| 5,117,825 A | 6/1992 | Grevious |
| 5,121,777 A | 6/1992 | Leininger et al. |
| 5,127,451 A | 7/1992 | Fink, Jr. et al. |
| 5,129,394 A | 7/1992 | Mehra |
| 5,129,806 A | 7/1992 | Hehl et al. |
| 5,131,145 A | 7/1992 | Badoureaux et al. |
| 5,131,388 A | 7/1992 | Pless et al. |
| 5,133,358 A | 7/1992 | Gustafson et al. |
| 5,135,488 A | 8/1992 | Foote et al. |
| 5,139,484 A | 8/1992 | Hazon et al. |
| 5,144,949 A | 9/1992 | Olson |
| 5,148,580 A | 9/1992 | Dyckow et al. |
| 5,148,695 A | 9/1992 | Ellis |
| 5,152,770 A | 10/1992 | Bengmark et al. |
| 5,152,776 A | 10/1992 | Pinchuk |
| 5,154,170 A | 10/1992 | Bennett et al. |
| 5,154,171 A | 10/1992 | Chirife et al. |
| 5,154,693 A | 10/1992 | East et al. |
| 5,156,972 A | 10/1992 | Issachar et al. |
| 5,158,078 A | 10/1992 | Bennett et al. |
| 5,163,429 A | 11/1992 | Cohen |
| 5,167,615 A | 12/1992 | East et al. |
| 5,168,757 A | 12/1992 | Rabenau et al. |
| 5,168,982 A | 12/1992 | Hakanen et al. |
| 5,171,299 A | 12/1992 | Heitzmann et al. |
| 5,173,873 A | 12/1992 | Wu et al. |
| 5,174,286 A | 12/1992 | Chirife et al. |
| 5,174,291 A | 12/1992 | Schoonen et al. |
| 5,176,502 A | 1/1993 | Sanderson et al. |
| 5,178,197 A | 1/1993 | Healy |
| 5,181,423 A | 1/1993 | Philipps et al. |
| 5,181,517 A | 1/1993 | Hickey |
| 5,184,132 A | 2/1993 | Baird |
| 5,184,614 A | 2/1993 | Collins et al. |
| 5,184,619 A | 2/1993 | Austin |
| 5,185,535 A | 2/1993 | Farb et al. |
| 5,186,224 A | 2/1993 | Schirmacher et al. |
| 5,188,106 A | 2/1993 | Nappholz et al. |
| 5,188,604 A | 2/1993 | Orth |
| 5,192,314 A | 3/1993 | Daskalakis |
| 5,195,362 A | 3/1993 | Eason |
| 5,197,322 A | 3/1993 | Indravudh |
| 5,199,427 A | 4/1993 | Strickland |
| 5,199,428 A | 4/1993 | Obel et al. |
| 5,201,753 A | 4/1993 | Lampropoulos et al. |
| 5,204,670 A | 4/1993 | Stinton |
| 5,207,429 A | 5/1993 | Walmsley et al. |
| 5,209,223 A | 5/1993 | McGorry et al. |
| 5,209,732 A | 5/1993 | Lampropoulos et al. |
| 5,211,129 A | 5/1993 | Taylor et al. |
| 5,211,161 A | 5/1993 | Stef et al. |
| 5,212,476 A | 5/1993 | Maloney |

(56) References Cited

U.S. PATENT DOCUMENTS

| | | |
|---|---|---|
| 5,213,331 A | 5/1993 | Avanzini |
| 5,215,523 A | 6/1993 | Williams et al. |
| 5,218,343 A | 6/1993 | Stobbe et al. |
| 5,218,957 A | 6/1993 | Strickland |
| 5,226,429 A | 7/1993 | Kuzmak |
| 5,226,604 A | 7/1993 | Seiffert et al. |
| 5,230,694 A | 7/1993 | Rosenblum |
| 5,233,985 A | 8/1993 | Hudrlik |
| 5,235,326 A | 8/1993 | Beigel et al. |
| 5,244,269 A | 9/1993 | Harriehausen et al. |
| 5,244,461 A | 9/1993 | Derlien et al. |
| 5,246,008 A | 9/1993 | Mueller |
| 5,249,858 A | 10/1993 | Nusser |
| 5,250,020 A | 10/1993 | Bley |
| 5,254,096 A | 10/1993 | Rondelet et al. |
| 5,256,157 A | 10/1993 | Samiotes et al. |
| 5,263,244 A | 11/1993 | Centa et al. |
| 5,263,981 A | 11/1993 | Polyak et al. |
| 5,267,940 A | 12/1993 | Moulder |
| 5,267,942 A | 12/1993 | Saperston |
| 5,269,891 A | 12/1993 | Colin et al. |
| 5,271,395 A | 12/1993 | Wahlstrand et al. |
| 5,274,859 A | 1/1994 | Redman et al. |
| 5,280,789 A | 1/1994 | Potts |
| 5,282,839 A | 2/1994 | Roline et al. |
| 5,282,840 A | 2/1994 | Hudrlik |
| 5,291,894 A | 3/1994 | Nagy et al. |
| 5,292,219 A | 3/1994 | Merin et al. |
| 5,295,967 A | 3/1994 | Rondelet et al. |
| 5,298,022 A | 3/1994 | Bernardi et al. |
| 5,298,884 A | 3/1994 | Gilmore et al. |
| 5,300,093 A | 4/1994 | Koestner et al. |
| 5,300,120 A | 4/1994 | Knapp et al. |
| 5,304,112 A | 4/1994 | Mrklas et al. |
| 5,305,923 A | 4/1994 | Kirschner et al. |
| 5,312,443 A | 5/1994 | Adams et al. |
| 5,312,452 A | 5/1994 | Salo |
| 5,312,453 A | 5/1994 | Shelton et al. |
| 5,313,953 A | 5/1994 | Yomtov et al. |
| 5,314,451 A | 5/1994 | Mulier |
| 5,314,457 A | 5/1994 | Jeutter et al. |
| 5,324,315 A | 6/1994 | Grevious |
| 5,325,834 A | 7/1994 | Ballheimer et al. |
| 5,326,249 A | 7/1994 | Weissfloch et al. |
| 5,328,460 A | 7/1994 | Lord et al. |
| 5,330,511 A | 7/1994 | Boute et al. |
| 5,337,750 A | 8/1994 | Walloch |
| 5,341,430 A | 8/1994 | Aulia et al. |
| 5,342,401 A | 8/1994 | Spano et al. |
| 5,342,406 A | 8/1994 | Thompson |
| 5,344,388 A | 9/1994 | Maxwell et al. |
| 5,347,476 A | 9/1994 | McBean, Sr. |
| 5,348,210 A | 9/1994 | Linzell et al. |
| 5,348,536 A | 9/1994 | Young et al. |
| 5,350,413 A | 9/1994 | Miller et al. |
| 5,352,180 A | 10/1994 | Candelon et al. |
| 5,353,622 A | 10/1994 | Theener |
| 5,353,800 A | 10/1994 | Pohndorf et al. |
| 5,354,200 A | 10/1994 | Klein et al. |
| 5,354,316 A | 10/1994 | Keimel |
| 5,354,319 A | 10/1994 | Wyborny et al. |
| 5,360,407 A | 11/1994 | Leonard et al. |
| 5,365,462 A | 11/1994 | McBean, Sr. |
| 5,365,619 A | 11/1994 | Solomon |
| 5,365,985 A | 11/1994 | Todd et al. |
| 5,368,040 A | 11/1994 | Carney |
| 5,370,665 A | 12/1994 | Hudrlik |
| 5,373,852 A | 12/1994 | Harrison et al. |
| 5,375,073 A | 12/1994 | McBean |
| 5,377,128 A | 12/1994 | McBean |
| 5,378,231 A | 1/1995 | Johnson et al. |
| 5,382,232 A | 1/1995 | Hague et al. |
| 5,383,915 A | 1/1995 | Adams |
| 5,388,578 A | 2/1995 | Yomtov et al. |
| 5,388,586 A | 2/1995 | Lee et al. |
| 5,388,831 A | 2/1995 | Quadri et al. |
| 5,394,909 A | 3/1995 | Mitchell et al. |
| 5,402,944 A | 4/1995 | Pape et al. |
| 5,406,957 A | 4/1995 | Tansey |
| 5,409,009 A | 4/1995 | Olson |
| 5,411,031 A | 5/1995 | Yomtov |
| 5,411,551 A | 5/1995 | Winston et al. |
| 5,411,552 A | 5/1995 | Andersen et al. |
| 5,416,372 A | 5/1995 | Ljungstroem et al. |
| 5,417,226 A | 5/1995 | Juma |
| 5,417,717 A | 5/1995 | Salo et al. |
| 5,425,362 A | 6/1995 | Siker et al. |
| 5,431,171 A | 7/1995 | Harrison et al. |
| 5,431,694 A | 7/1995 | Snaper et al. |
| 5,433,694 A | 7/1995 | Lim et al. |
| 5,437,605 A | 8/1995 | Helmy et al. |
| 5,443,215 A | 8/1995 | Fackler |
| 5,447,519 A | 9/1995 | Peterson |
| 5,449,368 A | 9/1995 | Kuzmak |
| 5,456,690 A | 10/1995 | Duong-Van |
| 5,461,390 A | 10/1995 | Hoshen |
| 5,464,435 A | 11/1995 | Neumann |
| 5,467,627 A | 11/1995 | Smith et al. |
| 5,474,226 A | 12/1995 | Joseph |
| 5,479,818 A | 1/1996 | Walter et al. |
| 5,482,049 A | 1/1996 | Addiss et al. |
| 5,487,760 A | 1/1996 | Villafana |
| 5,493,738 A | 2/1996 | Sanderson et al. |
| 5,494,036 A | 2/1996 | Uber, III et al. |
| 5,494,193 A | 2/1996 | Kirschner et al. |
| 5,504,474 A | 4/1996 | Libman et al. |
| 5,505,916 A | 4/1996 | Berry, Jr. |
| 5,507,412 A | 4/1996 | Ebert et al. |
| 5,507,737 A | 4/1996 | Palmskog et al. |
| 5,507,785 A | 4/1996 | Deno |
| 5,509,888 A | 4/1996 | Miller |
| 5,509,891 A | 4/1996 | DeRidder |
| 5,513,945 A | 5/1996 | Hartmann et al. |
| 5,514,103 A | 5/1996 | Srisathapat et al. |
| 5,518,504 A | 5/1996 | Polyak |
| 5,520,606 A | 5/1996 | Schoolman et al. |
| 5,523,740 A | 6/1996 | Burgmann et al. |
| 5,534,018 A | 7/1996 | Wahlstrand et al. |
| 5,535,752 A | 7/1996 | Halperin et al. |
| 5,538,005 A | 7/1996 | Harrison et al. |
| 5,541,857 A | 7/1996 | Walter et al. |
| 5,542,821 A | 8/1996 | Dugan |
| 5,545,140 A | 8/1996 | Conero et al. |
| 5,545,151 A | 8/1996 | O'Connor et al. |
| 5,545,186 A | 8/1996 | Olson et al. |
| 5,545,214 A | 8/1996 | Stevens |
| 5,547,470 A | 8/1996 | Johnson et al. |
| 5,551,427 A | 9/1996 | Altman |
| 5,551,439 A | 9/1996 | Hickey |
| 5,554,185 A | 9/1996 | Block et al. |
| 5,558,644 A | 9/1996 | Boyd et al. |
| 5,564,434 A | 10/1996 | Halperin et al. |
| 5,575,770 A | 11/1996 | Melsky et al. |
| 5,584,803 A | 12/1996 | Stevens et al. |
| 5,586,629 A | 12/1996 | Shoberg et al. |
| 5,593,430 A | 1/1997 | Renger |
| 5,594,665 A | 1/1997 | Walter et al. |
| 5,596,986 A | 1/1997 | Goldfarb |
| 5,597,284 A | 1/1997 | Weltlich et al. |
| 5,610,083 A | 3/1997 | Chan et al. |
| 5,611,768 A | 3/1997 | Tutrone, Jr. |
| 5,612,497 A | 3/1997 | Walter et al. |
| 5,615,671 A | 4/1997 | Schoonen et al. |
| 5,619,991 A | 4/1997 | Sloane |
| 5,625,946 A | 5/1997 | Wildeson et al. |
| 5,626,623 A | 5/1997 | Kieval et al. |
| 5,626,630 A | 5/1997 | Markowitz et al. |
| 5,630,836 A | 5/1997 | Prem et al. |
| 5,634,255 A | 6/1997 | Bishop et al. |
| 5,637,083 A | 6/1997 | Bertrand et al. |
| 5,643,207 A | 7/1997 | Rise |
| 5,645,116 A | 7/1997 | McDonald |
| 5,650,766 A | 7/1997 | Burgmann et al. |
| 5,673,585 A | 10/1997 | Bishop et al. |

(56) References Cited

U.S. PATENT DOCUMENTS

| | | |
|---|---|---|
| 5,676,690 A | 10/1997 | Noren et al. |
| 5,681,285 A | 10/1997 | Ford et al. |
| 5,686,831 A | 11/1997 | Vandervalk et al. |
| 5,687,734 A | 11/1997 | Dempsey et al. |
| 5,693,076 A | 12/1997 | Kaemmerer |
| 5,702,368 A | 12/1997 | Stevens et al. |
| 5,702,427 A | 12/1997 | Ecker et al. |
| 5,702,431 A | 12/1997 | Wang et al. |
| 5,704,352 A | 1/1998 | Tremblay et al. |
| 5,715,786 A | 2/1998 | Seiberth et al. |
| 5,715,837 A | 2/1998 | Chen |
| 5,720,436 A | 2/1998 | Buschor et al. |
| 5,730,101 A | 3/1998 | Aupperle et al. |
| 5,732,710 A | 3/1998 | Rabinovich et al. |
| 5,733,313 A | 3/1998 | Barreras, Sr. et al. |
| 5,738,652 A | 4/1998 | Boyd et al. |
| 5,742,233 A | 4/1998 | Hoffman et al. |
| 5,743,267 A | 4/1998 | Nikolic et al. |
| 5,749,369 A | 5/1998 | Rabinovich et al. |
| 5,749,909 A | 5/1998 | Schroeppel et al. |
| 5,755,687 A | 5/1998 | Donlon |
| 5,755,748 A | 5/1998 | Borza et al. |
| 5,765,568 A | 6/1998 | Sweezer, Jr. et al. |
| 5,769,812 A | 6/1998 | Stevens et al. |
| 5,771,903 A | 6/1998 | Jakobsson |
| 5,782,774 A | 7/1998 | Shmulewitz |
| 5,787,520 A | 8/1998 | Dunbar |
| 5,791,344 A | 8/1998 | Schulman et al. |
| 5,792,094 A | 8/1998 | Stevens et al. |
| 5,792,179 A | 8/1998 | Sideris |
| 5,795,325 A | 8/1998 | Valley et al. |
| 5,796,827 A | 8/1998 | Coppersmith et al. |
| 5,800,375 A | 9/1998 | Sweezer et al. |
| 5,807,265 A | 9/1998 | Itoigawa et al. |
| 5,807,336 A | 9/1998 | Russo et al. |
| 5,810,015 A | 9/1998 | Flaherty |
| 5,810,757 A | 9/1998 | Sweezer, Jr. et al. |
| 5,814,016 A | 9/1998 | Valley et al. |
| 5,817,093 A | 10/1998 | Williamson, IV et al. |
| 5,833,603 A | 11/1998 | Kovacs et al. |
| 5,836,300 A | 11/1998 | Mault |
| 5,836,886 A | 11/1998 | Itoigawa et al. |
| 5,840,081 A | 11/1998 | Andersen et al. |
| 5,849,225 A | 12/1998 | Ebina et al. |
| 5,855,597 A | 1/1999 | Jayaraman et al. |
| 5,855,601 A | 1/1999 | Bessler et al. |
| 5,860,938 A | 1/1999 | Lafontaine et al. |
| 5,861,018 A | 1/1999 | Feierbach |
| 5,863,366 A | 1/1999 | Snow |
| 5,868,702 A | 2/1999 | Stevens et al. |
| 5,873,837 A | 2/1999 | Lieber et al. |
| 5,875,953 A | 3/1999 | Shioya et al. |
| 5,879,499 A | 3/1999 | Corvi |
| 5,881,919 A | 3/1999 | Womac et al. |
| 5,885,238 A | 3/1999 | Stevens et al. |
| 5,887,475 A | 3/1999 | Muldner |
| 5,899,927 A | 5/1999 | Ecker et al. |
| 5,916,179 A | 6/1999 | Sharrock |
| 5,916,237 A | 6/1999 | Schu |
| 5,935,078 A | 8/1999 | Feierbach |
| 5,938,669 A | 8/1999 | Klaiber et al. |
| 5,951,487 A | 9/1999 | Brehmeier-Flick et al. |
| 5,957,861 A | 9/1999 | Combs et al. |
| 5,967,986 A | 10/1999 | Cimochowski et al. |
| 5,971,934 A | 10/1999 | Scherer et al. |
| 5,974,873 A | 11/1999 | Nelson et al. |
| 5,978,985 A | 11/1999 | Thurman |
| 5,995,874 A | 11/1999 | Borza et al. |
| 6,015,386 A | 1/2000 | Kensey et al. |
| 6,015,387 A | 1/2000 | Schwartz et al. |
| 6,019,729 A | 2/2000 | Itoigawa et al. |
| 6,024,704 A | 2/2000 | Meador et al. |
| 6,030,413 A | 2/2000 | Lazarus |
| 6,033,366 A | 3/2000 | Brockway et al. |
| 6,035,461 A | 3/2000 | Nguyen |
| 6,053,873 A | 4/2000 | Govari et al. |
| 6,056,723 A | 5/2000 | Donlon |
| 6,058,330 A | 5/2000 | Borza et al. |
| 6,059,757 A | 5/2000 | Macoviak et al. |
| 6,067,474 A | 5/2000 | Schulman et al. |
| 6,067,991 A | 5/2000 | Forsell et al. |
| 6,076,016 A | 6/2000 | Feierbach |
| 6,083,174 A | 7/2000 | Brehmeier-Flick et al. |
| 6,090,096 A | 7/2000 | St. Goar et al. |
| 6,102,678 A | 8/2000 | Peclat et al. |
| 6,102,856 A | 8/2000 | Groff et al. |
| 6,102,922 A | 8/2000 | Jakobsson et al. |
| 6,106,477 A | 8/2000 | Miesel et al. |
| 6,106,551 A | 8/2000 | Crossett et al. |
| 6,110,145 A | 8/2000 | Macoviak |
| 6,113,553 A | 9/2000 | Chubbuck |
| 6,131,664 A | 10/2000 | Sonnier |
| 6,135,945 A | 10/2000 | Sultan |
| 6,159,156 A | 12/2000 | Van Bockel et al. |
| 6,162,180 A | 12/2000 | Miesel et al. |
| 6,162,245 A | 12/2000 | Jayaraman et al. |
| 6,164,933 A | 12/2000 | Tani et al. |
| 6,168,614 B1 | 1/2001 | Andersen et al. |
| 6,234,745 B1 | 5/2001 | Pugh et al. |
| 6,240,316 B1 | 5/2001 | Richmond et al. |
| 6,240,318 B1 | 5/2001 | Phillips |
| 6,245,102 B1 | 6/2001 | Jayaraman |
| 6,248,080 B1 | 6/2001 | Miesel et al. |
| 6,251,093 B1 | 6/2001 | Valley et al. |
| 6,269,819 B1 | 8/2001 | Oz et al. |
| 6,277,078 B1 | 8/2001 | Porat et al. |
| 6,292,697 B1 | 9/2001 | Roberts |
| 6,309,350 B1 | 10/2001 | VanTassel et al. |
| 6,315,769 B1 | 11/2001 | Peer et al. |
| 6,319,208 B1 | 11/2001 | Abita et al. |
| 6,328,699 B1 | 12/2001 | Eigler et al. |
| 6,338,735 B1 | 1/2002 | Stevens |
| 6,357,438 B1 | 3/2002 | Hansen |
| 6,360,122 B1 | 3/2002 | Fischell et al. |
| 6,360,822 B1 | 3/2002 | Robertson et al. |
| 6,366,817 B1 | 4/2002 | Kung |
| 6,379,308 B1 | 4/2002 | Brockway et al. |
| 6,379,380 B1 | 4/2002 | Satz |
| 6,398,752 B1 | 6/2002 | Sweezer, Jr. et al. |
| 6,409,674 B1 | 6/2002 | Brockway et al. |
| 6,423,031 B1 | 7/2002 | Donlon |
| 6,430,444 B1 | 8/2002 | Borza et al. |
| 6,431,175 B1 | 8/2002 | Penner et al. |
| 6,432,040 B1 | 8/2002 | Meah |
| 6,443,887 B1 | 9/2002 | Derus et al. |
| 6,443,893 B1 | 9/2002 | Schnakenberg et al. |
| 6,450,173 B1 | 9/2002 | Forsell et al. |
| 6,450,946 B1 | 9/2002 | Forsell et al. |
| 6,453,907 B1 | 9/2002 | Forsell et al. |
| 6,454,698 B1 | 9/2002 | Forsell et al. |
| 6,454,699 B1 | 9/2002 | Forsell et al. |
| 6,454,700 B1 | 9/2002 | Forsell et al. |
| 6,454,701 B1 | 9/2002 | Forsell et al. |
| 6,461,292 B1 | 10/2002 | Forsell et al. |
| 6,461,293 B1 | 10/2002 | Forsell et al. |
| 6,463,329 B1 | 10/2002 | Goedeke |
| 6,463,935 B1 | 10/2002 | Forsell et al. |
| 6,464,628 B1 | 10/2002 | Forsell et al. |
| 6,470,212 B1 | 10/2002 | Weijand et al. |
| 6,470,892 B1 | 10/2002 | Forsell et al. |
| 6,471,635 B1 | 10/2002 | Forsell et al. |
| 6,475,136 B1 | 11/2002 | Forsell et al. |
| 6,475,170 B1 | 11/2002 | Doron et al. |
| 6,482,145 B1 | 11/2002 | Forsell et al. |
| 6,482,171 B1 | 11/2002 | Corvi et al. |
| 6,482,177 B1 | 11/2002 | Leinders et al. |
| 6,486,588 B2 | 11/2002 | Doron et al. |
| 6,503,189 B1 | 1/2003 | Forsell et al. |
| 6,504,286 B1 | 1/2003 | Porat et al. |
| 6,531,739 B2 | 3/2003 | Cable et al. |
| 6,533,719 B2 | 3/2003 | Kuyava et al. |
| 6,533,733 B1 | 3/2003 | Ericson et al. |
| 6,542,350 B1 | 4/2003 | Rogers |
| 6,558,321 B1 | 5/2003 | Burd et al. |

(56) References Cited

U.S. PATENT DOCUMENTS

| | | |
|---|---|---|
| 6,558,994 B2 | 5/2003 | Cha et al. |
| 6,573,563 B2 | 6/2003 | Lee et al. |
| 6,582,462 B1 | 6/2003 | Andersen et al. |
| 6,599,250 B2 | 7/2003 | Webb et al. |
| 6,605,112 B1 | 8/2003 | Moll et al. |
| 6,629,534 B1 | 10/2003 | St. Goar et al. |
| 6,640,137 B2 | 10/2003 | MacDonald |
| 6,641,610 B2 | 11/2003 | Wolf et al. |
| 6,645,143 B2 | 11/2003 | VanTassel et al. |
| 6,673,109 B2 | 1/2004 | Cox |
| 6,678,561 B2 | 1/2004 | Forsell |
| 6,682,480 B1 | 1/2004 | Habib et al. |
| 6,682,503 B1 | 1/2004 | Fariss et al. |
| 6,682,559 B2 | 1/2004 | Myers et al. |
| 6,695,866 B1 | 2/2004 | Kuehn et al. |
| 6,709,385 B2 | 3/2004 | Forsell et al. |
| 6,718,200 B2 | 4/2004 | Marmaropoulos et al. |
| 6,719,787 B2 | 4/2004 | Cox |
| 6,719,788 B2 | 4/2004 | Cox |
| 6,719,789 B2 | 4/2004 | Cox |
| 6,731,976 B2 | 5/2004 | Penn et al. |
| 6,733,525 B2 | 5/2004 | Yang et al. |
| 6,736,846 B2 | 5/2004 | Cox |
| 6,752,813 B2 | 6/2004 | Goldfarb et al. |
| 6,796,942 B1 | 9/2004 | Kreiner et al. |
| 6,822,343 B2 | 11/2004 | Estevez |
| 6,851,628 B1 | 2/2005 | Garrison et al. |
| 6,855,115 B2 | 2/2005 | Fonseca et al. |
| 6,889,772 B2 | 5/2005 | Buytaert et al. |
| 6,890,300 B2 | 5/2005 | Lloyd et al. |
| 6,896,651 B2 | 5/2005 | Gross et al. |
| 6,896,690 B1 | 5/2005 | Lambrecht et al. |
| 6,913,600 B2 | 7/2005 | Valley et al. |
| 6,915,165 B2 | 7/2005 | Forsell et al. |
| 6,926,246 B2 | 8/2005 | Ginggen et al. |
| 6,929,653 B2 | 8/2005 | Strecter |
| 6,932,792 B1 | 8/2005 | St. Goar et al. |
| 6,951,229 B2 | 10/2005 | Garrison et al. |
| 6,951,571 B1 | 10/2005 | Srivastava |
| 6,953,429 B2 | 10/2005 | Forsell et al. |
| 2,961,619 A1 | 11/2005 | Casey |
| 6,961,619 B2 | 11/2005 | Casey |
| 6,970,742 B2 | 11/2005 | Mann et al. |
| 6,979,350 B2 | 12/2005 | Moll et al. |
| 6,985,078 B2 | 1/2006 | Suzuki et al. |
| 6,989,027 B2 | 1/2006 | Allen et al. |
| 7,011,095 B2 | 3/2006 | Wolf et al. |
| 7,011,624 B2 | 3/2006 | Forsell et al. |
| 7,017,583 B2 | 3/2006 | Forsell et al. |
| 7,018,406 B2 | 3/2006 | Seguin et al. |
| 7,021,402 B2 | 4/2006 | Beato et al. |
| 7,025,727 B2 | 4/2006 | Brockway et al. |
| 7,044,920 B2 | 5/2006 | Letort |
| 7,060,080 B2 | 6/2006 | Bachmann et al. |
| 7,081,683 B2 | 7/2006 | Ariav et al. |
| 7,109,933 B2 | 9/2006 | Ito et al. |
| 7,131,447 B2 | 11/2006 | Sterman et al. |
| 7,131,945 B2 | 11/2006 | Fink et al. |
| 7,134,580 B2 | 11/2006 | Garrison et al. |
| 7,144,400 B2 | 12/2006 | Byrum et al. |
| 7,147,640 B2 | 12/2006 | Huebner et al. |
| 7,153,262 B2 | 12/2006 | Stivoric et al. |
| 7,187,978 B2 | 3/2007 | Malek et al. |
| 7,225,032 B2 | 5/2007 | Schmeling et al. |
| 7,257,438 B2 | 8/2007 | Kinast |
| 7,285,090 B2 | 10/2007 | Stivoric et al. |
| 7,397,166 B1 | 7/2008 | Morgan et al. |
| 8,057,492 B2 | 11/2011 | Ortiz et al. |
| 2001/0011543 A1 | 8/2001 | Forsell |
| 2001/0041823 A1 | 11/2001 | Snyder et al. |
| 2002/0049394 A1 | 4/2002 | Roy et al. |
| 2002/0120200 A1 | 8/2002 | Brockway et al. |
| 2002/0138009 A1 | 9/2002 | Brockway et al. |
| 2002/0177782 A1 | 11/2002 | Penner |
| 2003/0009201 A1 | 1/2003 | Forsell |
| 2003/0030893 A1 | 2/2003 | Cornelius et al. |
| 2003/0032857 A1 | 2/2003 | Forsell |
| 2003/0037591 A1 | 2/2003 | Ashton et al. |
| 2003/0045775 A1 | 3/2003 | Forsell |
| 2003/0066536 A1 | 4/2003 | Forsell |
| 2003/0088148 A1 | 5/2003 | Forsell |
| 2003/0092962 A1 | 5/2003 | Forsell |
| 2003/0093117 A1 | 5/2003 | Saadat |
| 2003/0100929 A1 | 5/2003 | Forsell |
| 2003/0105385 A1 | 6/2003 | Forsell |
| 2003/0109771 A1 | 6/2003 | Forsell |
| 2003/0114729 A1 | 6/2003 | Forsell |
| 2003/0125605 A1 | 7/2003 | Forsell |
| 2003/0125768 A1 | 7/2003 | Peter |
| 2003/0135089 A1 | 7/2003 | Forsell |
| 2003/0135090 A1 | 7/2003 | Forsell |
| 2003/0136417 A1 | 7/2003 | Fonseca et al. |
| 2003/0144648 A1 | 7/2003 | Forsell |
| 2003/0163079 A1 | 8/2003 | Burnett |
| 2003/0216666 A1 | 11/2003 | Ericson et al. |
| 2004/0054352 A1 | 3/2004 | Adams et al. |
| 2004/0068220 A1 | 4/2004 | Couvillon et al. |
| 2004/0113790 A1 | 6/2004 | Hamel et al. |
| 2004/0133092 A1 | 7/2004 | Kain |
| 2004/0147969 A1 | 7/2004 | Mann et al. |
| 2004/0172087 A1 | 9/2004 | Forsell |
| 2004/0186396 A1 | 9/2004 | Roy et al. |
| 2004/0254537 A1 | 12/2004 | Conlon et al. |
| 2005/0015014 A1 | 1/2005 | Fonseca et al. |
| 2005/0025979 A1 | 2/2005 | Sandt et al. |
| 2005/0027175 A1 | 2/2005 | Yang |
| 2005/0038328 A1 | 2/2005 | Stoehrer et al. |
| 2005/0061079 A1 | 3/2005 | Schulman |
| 2005/0102026 A1 | 5/2005 | Turner et al. |
| 2005/0159789 A1 | 7/2005 | Brockway et al. |
| 2005/0165317 A1 | 7/2005 | Turner et al. |
| 2005/0182330 A1 | 8/2005 | Brockway et al. |
| 2005/0187482 A1 | 8/2005 | O'Brien et al. |
| 2005/0187488 A1 | 8/2005 | Wolf |
| 2005/0192531 A1 | 9/2005 | Birk |
| 2005/0192642 A1 | 9/2005 | Forsell |
| 2005/0240155 A1 | 10/2005 | Conlon |
| 2005/0240156 A1 | 10/2005 | Conlon |
| 2005/0250979 A1 | 11/2005 | Coe |
| 2005/0267406 A1 | 12/2005 | Hassler |
| 2005/0267500 A1 | 12/2005 | Hassler et al. |
| 2005/0272968 A1 | 12/2005 | Byrum et al. |
| 2005/0277960 A1 | 12/2005 | Hassler et al. |
| 2005/0277974 A1 | 12/2005 | Hassler et al. |
| 2005/0288604 A1 | 12/2005 | Eigler et al. |
| 2005/0288720 A1 | 12/2005 | Ross et al. |
| 2005/0288721 A1 | 12/2005 | Girouard et al. |
| 2005/0288739 A1 | 12/2005 | Hassler et al. |
| 2005/0288740 A1 | 12/2005 | Hassler et al. |
| 2005/0288741 A1 | 12/2005 | Hassler et al. |
| 2005/0288742 A1 | 12/2005 | Giordano et al. |
| 2006/0002035 A1 | 1/2006 | Gao et al. |
| 2006/0010090 A1 | 1/2006 | Brockway et al. |
| 2006/0020224 A1 | 1/2006 | Geiger |
| 2006/0020305 A1 | 1/2006 | Desai et al. |
| 2006/0035446 A1 | 2/2006 | Chang et al. |
| 2006/0047205 A1 | 3/2006 | Ludomirsky et al. |
| 2006/0049714 A1 | 3/2006 | Liu et al. |
| 2006/0058627 A1 | 3/2006 | Flaherty et al. |
| 2006/0064134 A1 | 3/2006 | Mazar et al. |
| 2006/0085051 A1 | 4/2006 | Fritsch |
| 2006/0089571 A1 | 4/2006 | Gertner |
| 2006/0094966 A1 | 5/2006 | Brockway et al. |
| 2006/0100531 A1 | 5/2006 | Moser |
| 2006/0113187 A1 | 6/2006 | Deng et al. |
| 2006/0122285 A1 | 6/2006 | Falloon et al. |
| 2006/0122863 A1 | 6/2006 | Gottesman et al. |
| 2006/0142635 A1 | 6/2006 | Forsell |
| 2006/0149124 A1 | 7/2006 | Forsell |
| 2006/0149324 A1 | 7/2006 | Mann et al. |
| 2006/0149327 A1 | 7/2006 | Hedberg et al. |
| 2006/0157701 A1 | 7/2006 | Bauer et al. |
| 2006/0161186 A1 | 7/2006 | Hassler et al. |
| 2006/0178617 A1 | 8/2006 | Adams et al. |

(56) References Cited

U.S. PATENT DOCUMENTS

| | | |
|---|---|---|
| 2006/0178695 A1 | 8/2006 | Decant et al. |
| 2006/0183967 A1 | 8/2006 | Lechner |
| 2006/0184206 A1 | 8/2006 | Baker et al. |
| 2006/0189878 A1 | 8/2006 | Joshi et al. |
| 2006/0189887 A1* | 8/2006 | Hassler et al. ............... 600/561 |
| 2006/0189888 A1 | 8/2006 | Hassler, Jr. et al. |
| 2006/0189889 A1 | 8/2006 | Gertner |
| 2006/0199997 A1 | 9/2006 | Hassler et al. |
| 2006/0211912 A1 | 9/2006 | Dlugos et al. |
| 2006/0211913 A1 | 9/2006 | Dlugos et al. |
| 2006/0211914 A1 | 9/2006 | Hassler et al. |
| 2006/0217668 A1 | 9/2006 | Schulze et al. |
| 2006/0217673 A1 | 9/2006 | Schulze et al. |
| 2006/0235310 A1 | 10/2006 | O'Brien et al. |
| 2006/0235439 A1 | 10/2006 | Molitor et al. |
| 2006/0235448 A1 | 10/2006 | Roslin et al. |
| 2006/0244914 A1 | 11/2006 | Cech et al. |
| 2006/0247682 A1 | 11/2006 | Gerber et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0247723 A1 | 11/2006 | Gerber et al. |
| 2006/0247724 A1 | 11/2006 | Gerber et al. |
| 2006/0247725 A1 | 11/2006 | Gerber et al. |
| 2006/0252982 A1 | 11/2006 | Hassler et al. |
| 2006/0293625 A1 | 12/2006 | Hunt et al. |
| 2006/0293626 A1 | 12/2006 | Byrum et al. |
| 2006/0293627 A1 | 12/2006 | Byrum et al. |
| 2007/0010790 A1 | 1/2007 | Byrum et al. |
| 2007/0025868 A1* | 2/2007 | Swayze et al. ............... 417/474 |
| 2007/0027356 A1 | 2/2007 | Ortiz |
| 2007/0027493 A1 | 2/2007 | Ben-Haim et al. |
| 2007/0067206 A1 | 3/2007 | Haggerty et al. |
| 2007/0070906 A1 | 3/2007 | Thakur |
| 2007/0072452 A1 | 3/2007 | Inagaki et al. |
| 2007/0081304 A1 | 4/2007 | Takeguchi |
| 2007/0156013 A1 | 7/2007 | Birk |
| 2007/0161958 A1 | 7/2007 | Glenn |
| 2007/0167672 A1 | 7/2007 | Dlugos et al. |
| 2007/0173881 A1 | 7/2007 | Birk et al. |
| 2007/0179583 A1 | 8/2007 | Goetzinger et al. |
| 2007/0208313 A1 | 9/2007 | Conlon et al. |
| 2007/0225781 A1 | 9/2007 | Saadat et al. |
| 2007/0265645 A1* | 11/2007 | Birk et al. ............... 606/157 |
| 2008/0009680 A1 | 1/2008 | Hassler |
| 2008/0249806 A1 | 10/2008 | Dlugos et al. |
| 2008/0250341 A1 | 10/2008 | Dlugos et al. |
| 2009/0222065 A1 | 9/2009 | Dlugos, Jr. et al. |

FOREIGN PATENT DOCUMENTS

| | | |
|---|---|---|
| CA | 1275135 | 10/1990 |
| CA | 1277885 | 12/1990 |
| CA | 1317482 | 5/1993 |
| CA | 2082015 | 5/1993 |
| CA | 1327191 | 2/1994 |
| CA | 2119101 | 9/1994 |
| CA | 2305998 | 4/1999 |
| CN | 1059035 | 2/1992 |
| CN | 1119469 | 3/1996 |
| CN | 1241003 | 1/2000 |
| EA | 4581 | 6/2004 |
| EP | 125387 B1 | 11/1984 |
| EP | 417171 | 3/1991 |
| EP | 508141 | 10/1992 |
| EP | 568730 | 11/1993 |
| EP | 605302 | 7/1994 |
| EP | 660482 | 6/1995 |
| EP | 714017 | 5/1996 |
| EP | 769340 | 4/1997 |
| EP | 846475 | 6/1998 |
| EP | 848780 | 6/1998 |
| EP | 876808 | 11/1998 |
| EP | 888079 | 1/1999 |
| EP | 914059 | 5/1999 |
| EP | 0941712 A1 | 9/1999 |
| EP | 981293 | 3/2000 |
| EP | 997680 | 5/2000 |
| EP | 1003021 | 5/2000 |
| EP | 1022983 | 8/2000 |
| EP | 1050265 | 11/2000 |
| EP | 1115329 | 7/2001 |
| EP | 1119314 | 8/2001 |
| EP | 1128871 | 9/2001 |
| EP | 1202674 | 5/2002 |
| EP | 1213991 | 6/2002 |
| EP | 1253877 | 11/2002 |
| EP | 1253879 | 11/2002 |
| EP | 1253880 | 11/2002 |
| EP | 1253881 | 11/2002 |
| EP | 1253883 | 11/2002 |
| EP | 1253888 | 11/2002 |
| EP | 1255511 | 11/2002 |
| EP | 1255513 | 11/2002 |
| EP | 1255514 | 11/2002 |
| EP | 1263355 | 12/2002 |
| EP | 1263357 | 12/2002 |
| EP | 1284691 | 2/2003 |
| EP | 1374758 | 1/2004 |
| EP | 1488735 | 12/2004 |
| EP | 1500411 | 1/2005 |
| EP | 1510306 | 3/2005 |
| EP | 1518514 | 3/2005 |
| EP | 1545303 | 6/2005 |
| EP | 1547549 | 6/2005 |
| EP | 1563814 | 8/2005 |
| EP | 1568338 | 8/2005 |
| EP | 1582175 | 10/2005 |
| EP | 1582176 | 10/2005 |
| EP | 1584303 | 10/2005 |
| EP | 1586283 | 10/2005 |
| EP | 1591086 | 11/2005 |
| EP | 1593359 | 11/2005 |
| EP | 1598030 | 11/2005 |
| EP | 1609440 | 12/2005 |
| EP | 1674033 | 6/2006 |
| EP | 1736123 | 12/2006 |
| EP | 1799119 | 6/2007 |
| EP | 1815881 A1 | 8/2007 |
| EP | 1832252 A2 | 9/2007 |
| FR | 2730158 A1 | 8/1996 |
| GB | 2355937 | 5/2001 |
| RU | 2255712 C2 | 7/2005 |
| WO | WO-8911244 | 11/1989 |
| WO | WO-8911701 | 11/1989 |
| WO | WO-9004368 | 5/1990 |
| WO | WO-9511057 | 4/1995 |
| WO | WO-9715351 | 5/1997 |
| WO | WO-9733513 | 9/1997 |
| WO | WO-9833554 | 8/1998 |
| WO | WO-9835610 | 8/1998 |
| WO | WO-9901063 | 1/1999 |
| WO | WO-9918850 | 4/1999 |
| WO | 0009047 A1 | 2/2000 |
| WO | WO-0004945 | 2/2000 |
| WO | WO-0033738 | 6/2000 |
| WO | WO-0072899 | 12/2000 |
| WO | WO-0104487 | 1/2001 |
| WO | 0108597 A1 | 2/2001 |
| WO | WO-0112075 | 2/2001 |
| WO | WO-0112076 | 2/2001 |
| WO | WO-0112077 | 2/2001 |
| WO | WO-0112078 | 2/2001 |
| WO | WO-0121066 | 3/2001 |
| WO | WO-0136014 | 5/2001 |
| WO | WO-0145485 | 6/2001 |
| WO | WO-0145486 | 6/2001 |
| WO | WO-0147431 | 7/2001 |
| WO | WO-0147432 | 7/2001 |
| WO | WO-0147433 | 7/2001 |
| WO | WO-0147434 | 7/2001 |
| WO | WO-0147435 | 7/2001 |
| WO | WO-0147440 | 7/2001 |

(56) References Cited

FOREIGN PATENT DOCUMENTS

| | | |
|---|---|---|
| WO | WO-0147575 | 7/2001 |
| WO | WO-0148451 | 7/2001 |
| WO | WO-0149245 | 7/2001 |
| WO | WO-0150832 | 7/2001 |
| WO | WO-0150833 | 7/2001 |
| WO | WO-0154626 | 8/2001 |
| WO | WO-0158388 | 8/2001 |
| WO | WO-0158390 | 8/2001 |
| WO | WO-0158391 | 8/2001 |
| WO | WO-0158393 | 8/2001 |
| WO | WO-0160453 | 8/2001 |
| WO | WO-0181890 | 11/2001 |
| WO | WO-0200118 | 1/2002 |
| WO | WO-0215769 | 2/2002 |
| WO | WO-0226161 | 4/2002 |
| WO | WO-02053228 | 7/2002 |
| WO | WO-02055126 | 7/2002 |
| WO | WO-02058551 | 8/2002 |
| WO | WO-02065894 | 8/2002 |
| WO | WO-02076289 | 10/2002 |
| WO | WO-02082984 | 10/2002 |
| WO | WO-02089655 | 11/2002 |
| WO | WO-02090894 | 11/2002 |
| WO | WO-02100481 | 12/2002 |
| WO | WO-03002192 | 1/2003 |
| WO | WO-03002193 | 1/2003 |
| WO | WO-03020182 | 3/2003 |
| WO | WO-03061467 | 7/2003 |
| WO | WO-03061504 | 7/2003 |
| WO | WO-03096889 | 11/2003 |
| WO | 2004014245 A1 | 2/2004 |
| WO | WO-2004014456 | 2/2004 |
| WO | WO-2004019773 | 3/2004 |
| WO | WO-2004058101 | 7/2004 |
| WO | WO-2004066879 | 8/2004 |
| WO | WO-2004110263 | 12/2004 |
| WO | WO-2005000206 | 1/2005 |
| WO | WO-2005007075 | 1/2005 |
| WO | 2005/099618 A2 | 10/2005 |
| WO | WO-2005107583 | 11/2005 |
| WO | WO-2006001851 | 1/2006 |
| WO | WO-2006035446 | 4/2006 |
| WO | 06108203 A2 | 10/2006 |
| WO | WO-2006113187 | 10/2006 |
| WO | 2006118790 A2 | 11/2006 |
| WO | WO-2006122285 | 11/2006 |
| WO | 2007/030750 A1 | 3/2007 |
| WO | WO-2007067206 | 6/2007 |
| WO | WO-2007070906 | 6/2007 |
| WO | WO-2007072452 | 6/2007 |
| WO | WO-2007081304 | 7/2007 |
| WO | WO-2007104356 | 9/2007 |

OTHER PUBLICATIONS

European Search Report, Application No. 09250497.6, Issued Apr. 29, 2009, 5 pages.

"Application Specific Integrated Circuits (ASICs)", Honeywell product information from website http://www.honeywell.com/sites/portal?smap=aerospace&page=Radiation-Hardened-Electronics3&theme=T18&catID=CEO6BEF88-65F8-6A1E-4ED1-6A1EC1B7AE7A&id=HA0E380D3-C27B-9EBF-AAC8-9FAF8851256D&sel=1&sel4=1; 1 page.

"Rad Hard Aerospace Components Products", Honeywell product and service information from website http://www.honeywell.com/sites/portal?smap=aerospace&page=Radiation-Hardened-Electronics3&theme=T6&catID=C815147E4-8786-29FE-49EB-C21C8790AA99&id=H0166BA51-5344-E57E-5C37-C6333EA43F61&sel=1; 1 page.

"Radiation Hardened Electronics and Radiation Technology", Honeywell product and service information from website http://www.honeywell.com/sites/portal?smap=aerospace&page=Radiation-Hardened-Electronics&theme=T4; 2 pages.

Kirchner, G., "Honeywell and Synopsys: Concept-to-Parts Solutions for Next Generation Rad-Hard ASICs", in online magazine Compiler, http://www.synopsys.com/news/pubs/compiler/artlead_redasic-apr05.html, Apr. 2005, 5 pages.

P.A. Neukomm and H. Kundig, "Passive Wireless Actuator Control and Sensor Signal Transmission," Sensors and Actuators, A21-A23 (1990) 258-262.

European Search Report for Application No. 09250333.3, issued Jan. 28, 2013. (5 pages).

European Office Action for Application No. 09250334.1, issued Jan. 25, 2013.

Russian Decision on Grant for Application No. 2009104685, issued Apr. 2013.

Russian Office Action for Application No. 2009104686, issued Dec. 2012.

\* cited by examiner

AUTOMATICALLY ADJUSTING BAND SYSTEM

FIELD OF THE INVENTION

The present invention relates to implantable medical devices, and in particular implantable gastric restriction devices.

BACKGROUND OF THE INVENTION

Obesity is becoming a growing concern, particularly in the United States, as the number of obese people continues to increase, and more is learned about the negative health effects of obesity. Morbid obesity, in which a person is 100 pounds or more over ideal body weight, in particular poses significant risks for severe health problems. Accordingly, a great deal of attention is being focused on treating obese patients. One method of treating morbid obesity has been to place a restriction device, such as an elongated band, about the upper portion of the stomach. Gastric bands have typically comprised a fluid-filled elastomeric balloon with fixed endpoints that encircles the stomach just inferior to the esophageal-gastric junction to form a small gastric pouch above the band and a reduced stoma opening in the stomach. When fluid is infused into the balloon, the band expands against the stomach creating a food intake restriction or stoma in the stomach. To decrease this restriction, fluid is removed from the band. The effect of the band is to reduce the available stomach volume and thus the amount of food that can be consumed before becoming "full."

Food restriction devices have also comprised mechanically adjusted bands that similarly encircle the upper portion of the stomach. These bands include any number of resilient materials or gearing devices, as well as drive members, for adjusting the bands. Additionally, gastric bands have been developed that include both hydraulic and mechanical drive elements. An example of such an adjustable gastric band is disclosed in U.S. Pat. No. 6,067,991, entitled "Mechanical Food Intake Restriction Device" which issued on May 30, 2000, and is incorporated herein by reference. It is also known to restrict the available food volume in the stomach cavity by implanting an inflatable elastomeric balloon within the stomach cavity itself. The balloon is filled with a fluid to expand against the stomach walls and, thereby, decrease the available food volume within the stomach.

With each of the above-described food restriction devices, safe, effective treatment requires that the device be regularly monitored and adjusted to vary the degree of restriction applied to the stomach. With banding devices, the gastric pouch above the band will substantially increase in size following the initial implantation. Accordingly, the stoma opening in the stomach must initially be made large enough to enable the patient to receive adequate nutrition while the stomach adapts to the banding device. As the gastric pouch increases in size, the band may be adjusted to vary the stoma size. In addition, it is desirable to vary the stoma size in order to accommodate changes in the patient's body or treatment regime, or in a more urgent case, to relieve an obstruction or severe esophageal dilatation. Traditionally, adjusting a hydraulic gastric band required a scheduled clinician visit during which a Huber needle and syringe were used to penetrate the patient's skin and add or remove fluid from the balloon via an injection port. More recently, implantable pumps have been developed which enable non-invasive adjustments of the band. An external programmer communicates with the implanted pump using telemetry to control the pump. During a scheduled visit, a physician places a handheld portion of the programmer near the gastric implant and transmits power and command signals to the implant. The implant in turn adjusts the fluid levels in the band and transmits a response command to the programmer.

During these gastric band adjustments, it has been difficult to determine how the adjustment is proceeding, and whether the adjustment will have the intended effect. In an attempt to determine the efficacy of an adjustment, some physicians have utilized fluoroscopy with a Barium swallow as the adjustment is being performed. However, fluoroscopy is both expensive and undesirable due to the radiation doses incurred by both the physician and patient. Other physicians have instructed the patient to drink a glass of water during or after the adjustment to determine whether the water can pass through the adjusted stoma. This method, however, only assures that the patient is not obstructing, and does not provide any information about the efficacy of the adjustment. Oftentimes, a physician may simply adopt a "try as you go" method based upon their prior experience, and the results of an adjustment may not be discovered until hours or days later, when the patient experiences a complete obstruction to the stomach cavity, or the band induces erosion of the stomach tissue due to excessive interface pressures against the band.

Furthermore, the implantable pumps known in the art, such as centrifugal or positive displacement pumps, have high power requirements during operation. The power requirements of such pumps limit their usage for frequent adjustments to fluid levels in the band. Current pumps also require large housings to encase the mechanical pumping mechanism, gears, and motors, further limiting their usefulness as implantable pumps. Additional components, such as valves, are also necessary to maintain fluid pressure in the band when power is not supplied to conventional pumps. An example of an implantable pump system is described in US Patent Publication No. 2005/0277974, entitled "Thermodynamically driven reversible infuser pump for use as a remotely controlled gastric band" which was filed on May 28, 2004.

Accordingly, methods and devices are provided for use with a gastric restriction device, and in particular methods and devices are provided which allow adjustment of a gastric restriction device.

SUMMARY OF THE INVENTION

The present invention generally provides systems and methods for forming a restriction in a patient. In one exemplary embodiment, a restriction system includes an implantable restriction device and an implantable pump in fluid communication with the restriction device. Optionally, an implantable port can be in fluid communication with the implantable restriction device and the pump. The implantable restriction device is adjustable and configured to form a restriction in a patient, and the implantable port, if present, is configured to receive fluid from a fluid source external to the patient. The implantable pump has a plurality of actuators configured to change shape upon the application of energy thereto such that sequential activation of the plurality of actuators is effective to create pumping action to move fluid through the pump. Fluid in the restriction system can move in a direction from the pump to the restriction device or in a direction from the restriction device to the pump. In one embodiment, the pump can be in fluid communication with the implantable port. The system can also include an implantable sensor in communication with the restriction device and configured to measure at least a pressure within the restriction device. The restriction system can optionally include a fluid reservoir in fluid communication with the pump. The fluid reservoir is configured to hold fluid and can be configured to hold in the range of approximately 0.1 to 20 ml of fluid.

The implantable pump and its plurality of actuators can be arranged in a variety of configurations. In one exemplary embodiment the pump includes a first member having a passageway formed therethrough and being in communication with the plurality of actuators. The actuators can be disposed within the first member or outside the first member. At least one actuator can be configured to expand or contract (e.g., radially or axially) upon the application of energy thereto, and each of the actuators can be configured to move sequentially or independently. In one embodiment, at least one of the actuators can serve as a valve that is able to selectively control the passage of fluid by permitting, preventing, or limiting the passage of fluid. In one exemplary embodiment each actuator comprises an electroactive polymer.

The pump can be manually activated to move fluid either toward or away from the restriction device. Alternatively, the pump can be automatically activated, such as by techniques including timer control, or programmed to be activated in response to certain sensed parameters. In one embodiment, the implantable pump effects a pressure change within the restriction device in accordance with a programmed schedule.

Further disclosed herein are methods for adjusting pressure in an implantable restriction device. In one embodiment, the method can include sensing a clinically relevant parameter, adjusting a pressure within the restriction device in response to the sensed clinically relevant parameter by activating a pump in fluid communication with the restriction device. In one embodiment, the pump can be formed of a plurality of actuators configured to change shape upon the application of energy thereto such that sequential activation of the plurality of actuators is effective to create pumping action to move fluid through the pump. The sensing of the clinically relevant parameter can be effected using an implantable sensor. The clinically relevant parameter can be a pressure, in which case, the implantable sensor is a pressure sensor. In such an embodiment, the sensed pressure is compared to a desired pressure range and the pressure within the restriction device is adjusted to be approximately within the desired pressure range if the sensed pressure is not within a desired pressure range. In one embodiment, the pump can be automatically activated, although other activation techniques, including manual activation, are also envisioned.

Also disclosed herein is a pumping device including a fluid conduit member having a passageway formed therethrough, and a plurality of orientation-changing actuators disposed within the fluid conduit member. Each actuator is independently configurable between a normal, relaxed state in which the actuator occludes a portion of the passageway of the fluid conduit member and an energized configuration in which fluid flow is permitted between an outer surface of the actuator and an inner surface of the fluid conduit member. The actuators are also configured to change orientation upon the application of energy thereto such that sequential activation of the plurality of actuators is effective to create pumping action to move fluid through the first member.

The actuators can be formed from a variety of materials. In one exemplary embodiment, each actuator comprises an electroactive polymer (EAP). For example, each actuator can include a least one electroactive polymer composite having at least one flexible conductive layer, an electroactive polymer layer, and an ionic gel layer. Each actuator can also include a return electrode and a delivery electrode coupled thereto, the delivery electrode being adapted to deliver energy from an energy source. The actuators can be configured to move independently or sequentially.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides systems and methods for forming a restriction in a patient. In general, the systems and methods allow the pressure or volume of fluid in a restriction device to be adjusted. The pressure or volume adjustment is effected by the use of an implantable pump. The implantable pump allows the pressure or volume of fluid in a restriction device to be adjusted without the need for fluid to be added from an external source.

Figure 1A:
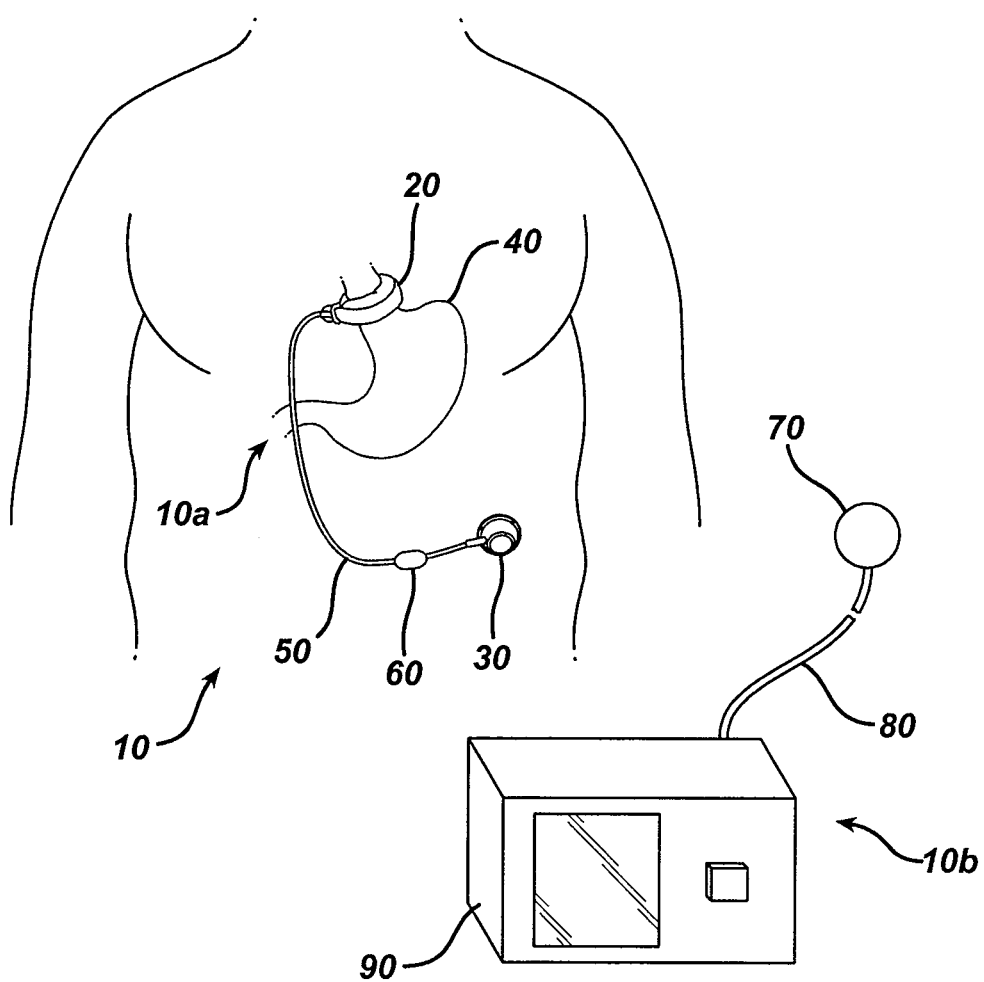
FIG. 1A is a schematic diagram of an embodiment of a food intake restriction system.
Figure 1B:
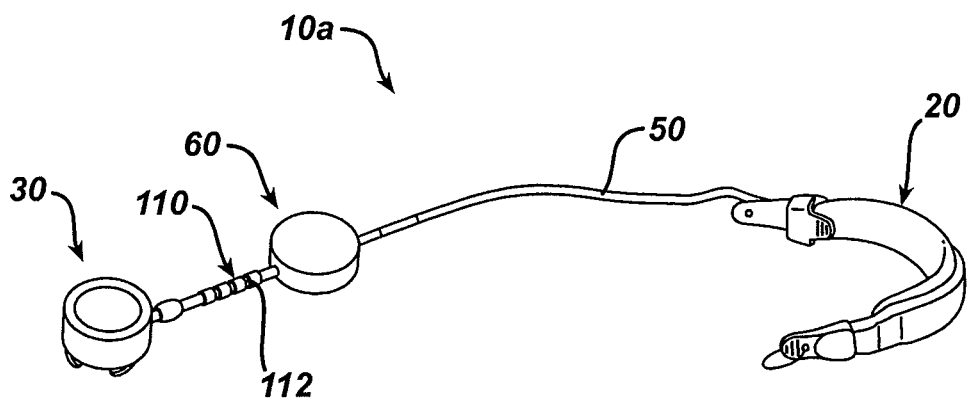
FIG. 1B is a perspective view of an embodiment of an implantable portion of the food intake restriction system of FIG. 1A.

While the present invention can be used with a variety of restriction systems known in the art, FIG. 1A illustrates one exemplary embodiment of a food intake restriction system 10 in use in a patient. As shown, the system 10 generally includes an implantable portion 10a and an external portion 10b. FIG. 1B illustrates the implantable portion 10a outside of a patient. The implantable portion 10a includes an adjustable gastric band 20 that is configured to be positioned around the upper portion of a patient's stomach 40, and an injection port housing 30 that is fluidly coupled to the adjustable gastric band 20, e.g., via a catheter 50.

The injection port housing 30 is adapted to allow fluid to be introduced into and removed from the gastric band 20 to thereby adjust the size of the band, and thus the pressure applied to the stomach. The injection port housing 30 can thus be implanted at a location within the body that is accessible through the tissue. Typically, injection ports are positioned in the lateral subcostal region of the patient's abdomen under the skin and layers of fatty tissue. Surgeons also typically implant injection ports on the sternum of the patient.

The internal portion 10a can also include a sensing or measuring device in fluid communication with the closed fluid circuit in the implantable portion 10a such that the measuring device can take measurements related to any parameter relevant to implantable restriction devices. Such clinically relevant parameters include, but are not limited to, temperature, pressure, changes in pressure, acoustic input, tissue impedance, changes in sensed tissue impedance, chemical composition, changes in chemical composition, pulse count, pulse width and amplitude. While the methods and devices discussed herein can relate to any sensed data parameter, in an exemplary embodiment, the measurements relate to pressure, and the methods and devices disclosed herein will be discussed in the context of measuring the fluid pressure of the closed fluid circuit. While the measuring device can have various configurations and it can be positioned anywhere along the internal portion 10a, including within the injection port housing 30, in the illustrated embodiment the measuring device is in the form of a pressure sensor that is disposed within a sensor housing 60 positioned adjacent to the injection port housing 30. The catheter 50 can include a first portion that is coupled between the gastric band 20 and the sensor housing 60, and a second portion that is coupled between the sensor housing 60 and the injection port housing 30.

In addition to sensing pressure of fluid within the internal portion 10a, pressure of fluid within the esophagus and/or the stomach 40 can also be sensed using any suitable device, such as an endoscopic manometer. By way of non-limiting example, such fluid pressure measurements can be compared against measured pressure of fluid within the internal portion 10a before, during, and/or after adjustment of pressure within the internal portion 10a. Other suitable uses for measured pressure within the esophagus and/or the stomach 40 will be appreciated by those skilled in the art.

As further shown in FIG. 1A, the external portion 10b generally includes a pressure reading device 70 that is configured to be positioned on the skin surface above the sensor housing 60 (which can be implanted beneath thick tissue, e.g., over 10 cm thick) to non-invasively communicate with the sensor housing 60 and thereby obtain pressure measurements. The pressure reading device 70 can optionally be electrically coupled (in this embodiment via an electrical cable assembly 80) to a control box 90 that can display the pressure measurements, or other data obtained from the pressure reading device 70.

FIG. 1B shows the implantable portion 10a in more detail. In the illustrated embodiment, the implantable portion 10a includes an adjustable gastric band 20, an injection port housing 30 that is fluidly coupled to the adjustable gastric band 20, a sensor housing 60, and a pump 110. The pump 110 can have a variety of configurations which will be discussed in more detail below. In the embodiment shown in FIG. 1B, the pump 110 generally includes an elongate member 112.

Figure 2A:
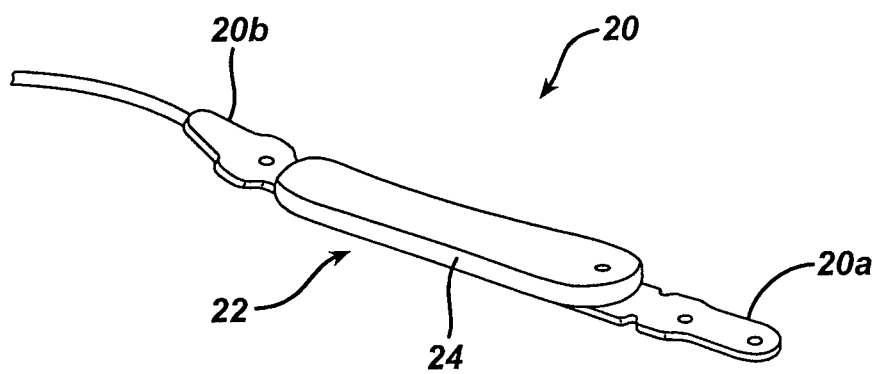
FIG. 2A is a perspective view of the food intake restriction device of FIG. 1A.

FIG. 2A shows the gastric band 20 in more detail. While the gastric band 20 can have a variety of configurations, and various gastric bands currently known in the art can be used with the present invention, in the illustrated embodiment the gastric band 20 has a generally elongate shape with a support structure 22 having first and second opposite ends 20a, 20b that can be secured to each other. Various mating techniques can be used to secure the ends 20a, 20b to one another. In the illustrated embodiment, the ends 20a, 20b are in the form of straps that mate together, with one laying on top of the other. The gastric band 20 can also include a variable volume member, such as an inflatable balloon 24, that is disposed or formed on one side of the support structure 22, and that is configured to be positioned adjacent to tissue. The balloon 24 can expand or contract against the outer wall of the stomach to form an adjustable stoma for controllably restricting food intake into the stomach.

A person skilled in the art will appreciate that the gastric band can have a variety of other configurations, moreover the various methods and devices disclosed herein have equal applicability to other types of implantable bands. For example, bands are used for the treatment of fecal incontinence, as described in U.S. Pat. No. 6,461,292 which is hereby incorporated herein by reference. Bands can also be used to treat urinary incontinence, as described in U.S. Patent Application 2003/0105385 which is hereby incorporated herein by reference. Bands can also be used to treat heartburn and/or acid reflux, as disclosed in U.S. Pat. No. 6,470,892 which is hereby incorporated herein by reference. Bands can also be used to treat impotence, as described in U.S. Patent Application 2003/0114729 which is hereby incorporated herein by reference.

Figure 2B:
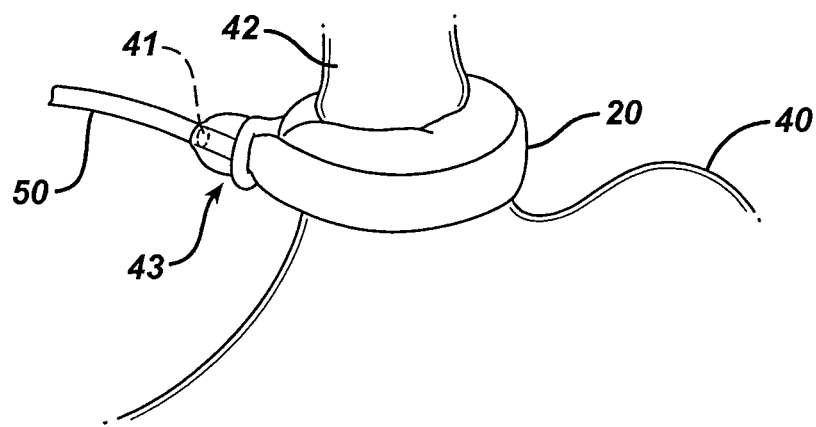
FIG. 2B is a schematic diagram of the food intake restriction device of FIG. 2A applied about the gastro-esophageal junction of a patient.

FIG. 2B shows the adjustable gastric band 20 applied about the gastro-esophageal junction of a patient. As shown, the band 20 at least substantially encloses the upper portion of the stomach 40 near the junction with the esophagus 42. After the band 20 is implanted, preferably in the deflated configuration wherein the band 20 contains little or no fluid, the band 20 can be inflated, e.g., using saline, to decrease the size of the stoma opening. A person skilled in the art will appreciate that various techniques, including mechanical and electrical techniques, can be used to adjust the band. FIG. 2B also shows an alternate location of a pressure sensor 41, disposed in a buckle 43 of the band 20.

Figure 3:
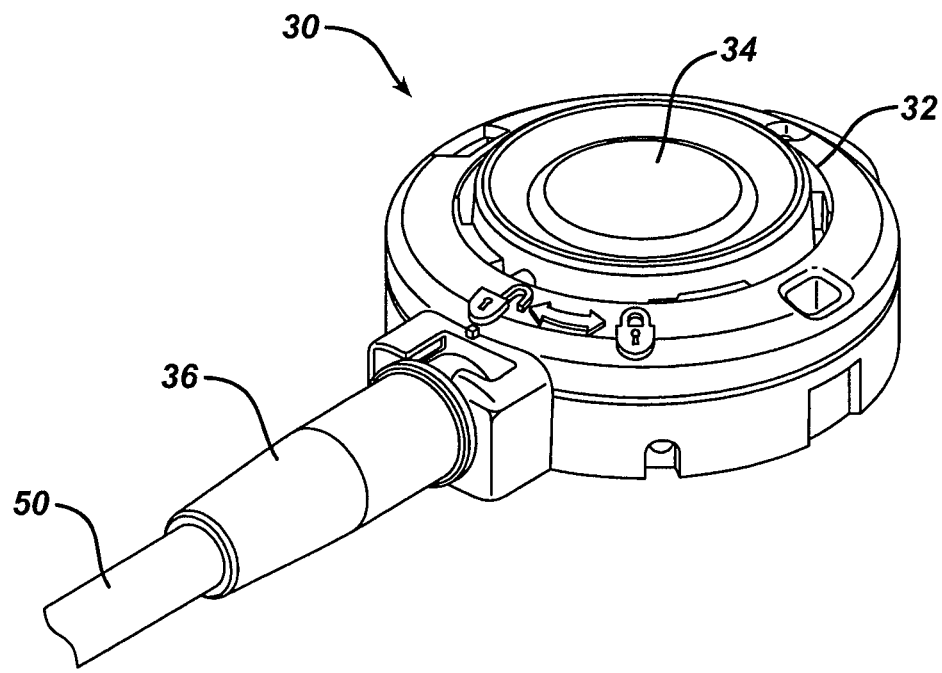
FIG. 3 is a perspective view of an embodiment of the injection port housing of FIG. 1A.

The fluid injection port housing 30 can also have a variety of configurations. In the embodiment shown in FIG. 3, the injection port housing 30 has a generally cylindrical shape with a distal or bottom surface and a perimeter wall extending proximally from the bottom surface and defining a proximal opening 32. The proximal opening 32 can include a needlepenetrable septum 34 extending there across and providing access to a fluid reservoir (not visible in FIG. 3) formed within the housing. The septum 34 is preferably placed in a proximal enough position such that the depth of the reservoir is sufficient enough to expose the open tip of a needle, such as a Huber needle, so that fluid transfer can take place. The septum 34 is preferably arranged so that it will self seal after being punctured by a needle and the needle is withdrawn. As further shown in FIG. 3, the port 30 can further include a catheter tube connection member 36 that is in fluid communication with the reservoir and that is configured to couple to a catheter (e.g., the catheter 50). A person skilled in the art will appreciate that the housing can be made from any number of materials, including stainless steel, titanium, or polymeric materials, and the septum 34 can likewise be made from any number of materials, including silicone.

Figure 4:
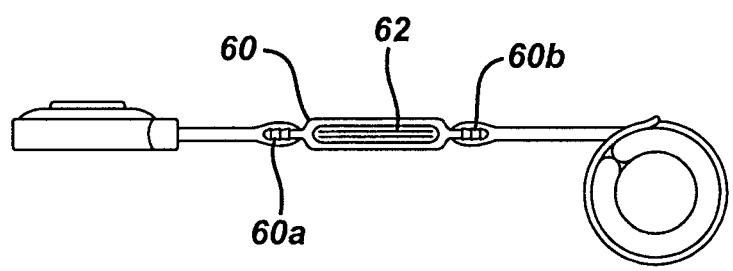
FIG. 4 is a perspective view of an embodiment of the sensor housing of FIG. 1A.

As indicated above, the system 10 can also include a pressure measuring device in communication with the closed fluid circuit and configured to measure pressure (e.g., fluid pressure) which corresponds to the amount of restriction applied by the adjustable gastric band 20 to the patient's stomach 40. Measuring the pressure enables a person (e.g., a physician, a nurse, a patient, etc.) to evaluate the efficacy and functionality of the restriction created by a band adjustment. In the illustrated embodiment, as shown in FIG. 4, the pressure measuring device is in the form of a pressure sensor 62 disposed within the sensor housing 60. The pressure measuring device can, however, be disposed anywhere within the closed hydraulic circuit of the implantable portion, and various exemplary locations and configurations are disclosed in more detail in commonly-owned U.S. Publication No. 2006/0211913 entitled "Non-Invasive Pressure Measurement In a Fluid Adjustable Restrictive Device," filed on Mar. 7, 2006, and hereby incorporated by reference.

In general, the illustrated sensor housing 60 includes an inlet 60a and an outlet 60b that are in fluid communication with the fluid in the implantable portion 10a. An already-implanted catheter 50 can be retrofitted with the sensor housing 60, such as by severing the catheter 50 and inserting barbed connectors (or any other connectors, such as clamps, clips, adhesives, welding, etc.) into the severed ends of the catheter 50. The sensor 62 can be disposed within the housing 60 and be configured to respond to fluid pressure changes within the hydraulic circuit and convert the pressure changes into a usable form of data. The pressure sensor 62 disposed within the housing 60 can sense and monitor the adjusted state of the band statically or while fluid is being pumped.

While not shown, the pressure sensing system can also include a microcontroller, a TET/telemetry coil, and a capacitor. Optionally, the pressure sensing system can further comprise a temperature sensor (not shown). The microcontroller, TET/telemetry coil, and capacitor can be in communication via a circuit board (not shown) or any via any other suitable component(s). It will also be appreciated that TET/telemetry coil and capacitor may collectively form a tuned tank circuit for receiving power from external portion, and transmitting the pressure measurement to the pressure reading device.

Various pressure sensors known in the art can be used, such as a wireless pressure sensor provided by CardioMEMS, Inc. of Atlanta, Ga., though a suitable MEMS pressure sensor may be obtained from any other source, including but not limited to Integrated Sensing Systems (ISSYS), and Remon Medical. One exemplary MEMS pressure sensor is described in U.S. Pat. No. 6,855,115, the disclosure of which is incorporated by reference herein for illustrative purposes only. It will also be appreciated that suitable pressure sensors may include, but are not limited to, capacitive, piezoresistive, silicon strain gauge, or ultrasonic (acoustic) pressure sensors, as well as various other devices capable of measuring pressure.

The pressure reading device 70 can also have a variety of configurations, and one exemplary pressure reading device is disclosed in more detail in commonly-owned U.S. Patent Application Publication No. 2006/0189888 and U.S. Patent Application Publication No. 2006/0199997, each of which is hereby incorporated by reference in its entirety. In general, the pressure reading device 70 can non-invasively measure the pressure of the fluid within implanted portion even when the injection port housing 30 or sensor housing 60 is implanted beneath thick (at least over 10 centimeters) subcutaneous fat tissue. The physician may hold pressure-reading device 70 against the patient's skin near the location of sensor and observe the pressure reading on a display on the control box 90. The pressure reading device 70 can also be removably attached to the patient, such as during a prolonged examination, using straps, adhesives, and other well-known methods. The pressure reading device 70 can operate through conventional cloth or paper surgical drapes, and can also include a disposable cover (not shown) that may be replaced for each patient.

Figure 5:
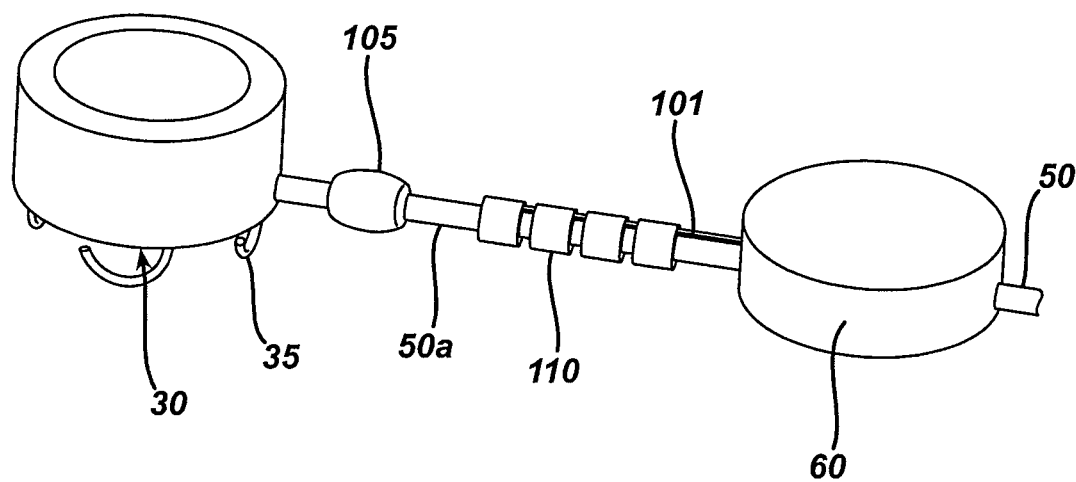
FIG. 5 is a perspective view of an implantable portion of the food intake restriction system according to one embodiment of the invention.

FIG. 5 illustrates one embodiment of the proximal end of the implantable portion 10a (FIGS. 1A and 1B) of the implantable restriction system 10. As shown, the proximal end of the implantable portion 10a includes an injection port housing 30, which is in fluid communication with a reservoir 105 and a pump 110. The proximal end may also include a sensor housing 60, as well as one or more sensor/power leads 101. Conduit 50a provides fluid communication between the individual components of the proximal end of the implantable portion 10a. Catheter 50 provides fluid communication between the proximal end of the implantable portion 10a shown in FIG. 5 and downstream restriction device 20 (FIG. 1B). Although the components shown in FIG. 5 are shown in an inline configuration, one skilled in the art will appreciate that the components can be connected in any order and in any configuration, i.e., in a T configuration or a Y configuration, for example.

As shown in FIG. 5, the injection port housing 30, if present, can optionally include an anchoring device, such as hooks 35, that can be used to anchor the injection port housing 30 within the patient's body. Although FIG. 5 shows that the housing 30 is arranged in line with the reservoir 105, the pump 110 and the sensor housing 60, the housing 30 can be connected to the other components and conduit 50a in other ways, i.e., in a T configuration or a Y configuration, for example. The injection port housing 30 itself is optional because the implantable restriction system 10a (FIG. 1B) can be filled with fluid prior to implantation or at the time of implantation. The pressure in the downstream restriction device 20 (FIG. 1B) can then be adjusted using the pump 110 to move fluid into or out of the restriction device 20.

Reservoir 105 provides an optional means for holding an additional supply of fluid. For example, the reservoir 105 can contain 0.1-20 ml of fluid. As shown, the reservoir 105 can be a portion of conduit 50a with a larger diameter than the nominal diameter of the conduit 50a. Various other configurations can be used to provide a reservoir 105, such as separate reservoir components connected to, and in fluid communication with, the conduit 50a or any other components, i.e., the injection port housing 30, the pump 110 or the sensor housing 60. Although FIG. 5 shows that the reservoir 105 is arranged in line between the pump 110 and the injection port housing 60, one skilled in the art will appreciate that the reservoir 105 can be connected to the other components and conduit 50a in other ways, i.e., in a T configuration or a Y configuration, for example. It will also be appreciated that the reservoir 105 need not necessarily contain enough fluid to fill and empty the entire band 20 (FIGS. 1A and 1B). For example, during the first fills of the band 20, fluid may be delivered via an injection through the injection port housing 30. During this time the pump 110 can be retained in an open position. Alternatively, the reservoir 105 can be filled and then the fluid can be delivered to the band 20 by the pump 110. Once the band 20 is at functional fullness, i.e., occluding the stomach enough to cause a restriction of intake, the reservoir 105 can be filled with enough fluid to accommodate future fill and adjustment needs without the need to add additional fluid via an injection port housing 30. One skilled in the art will appreciate that the reservoir 105 is optional, and in an embodiment without reservoir 105, not shown, the conduit 50a can optionally contain enough fluid to allow adjustments to the amount of fluid in the band 20.

The embodiment shown in FIG. 5 includes an optional sensor housing 60 that is disposed in fluid communication with the components of the proximal end of the implantable portion 10a (FIG. 1B). Although FIG. 5 shows that the sensor housing 60 is arranged inline with the catheter 50 and the conduit 50a, one skilled in the art will appreciate that the sensor housing 60 can be connected to the other components in other ways, i.e., in a T configuration or a Y configuration, for example. Alternatively, a sensor can be placed in other locations in the system, such as on the band itself. Sensor/power leads 101 can provide a connection between the sensor housing 60 and the pump 110 to supply energy to the pump, as will be discussed in more detail below.

The implantable pump 110 functions to move fluid into and out of the band 20 to increase or decrease pressure within the band as needed. Although the pump can have a variety of configurations, in one example the pump is based upon electroactive polymer (EAP) technology as discussed in more detail below. The use of EAP technology to form an implantable pump 110 provides a number of advantages, such as small size, low voltage requirements, high power density, and simplicity in terms of the number of moving parts.

Figure 6A:
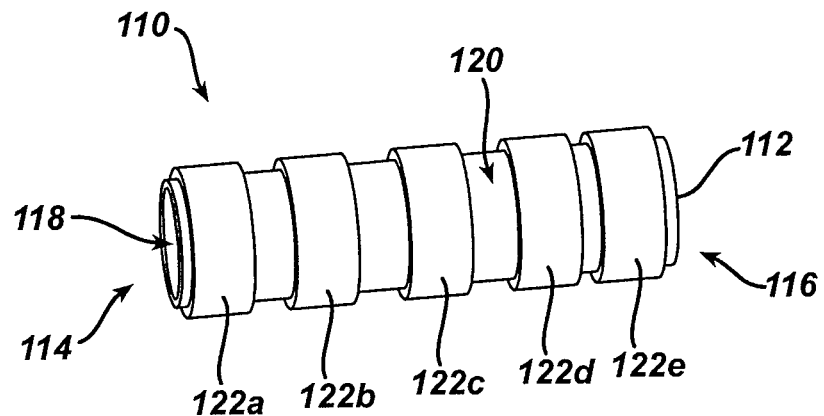
FIG. 6A is a perspective view of one exemplary embodiment of a pump having multiple actuators disposed around a flexible tube.
Figure 6B:
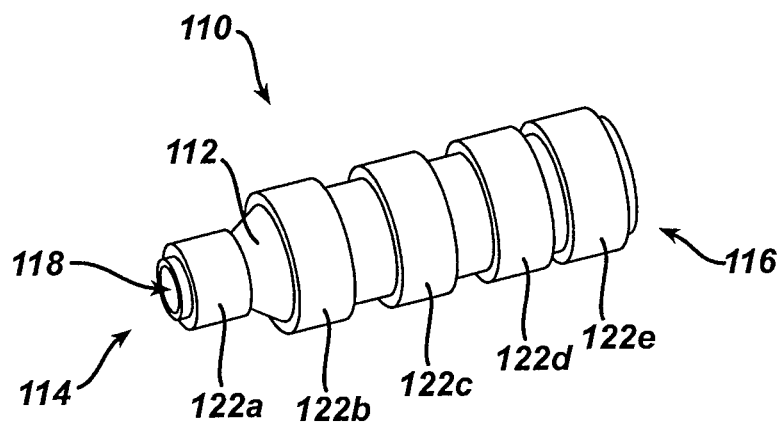
FIG. 6B is a perspective view of the pump of FIG. 6A with the first actuator activated.

FIG. 6A illustrates one exemplary embodiment of a pumping mechanism using EAP actuators. As shown, the pump 110 generally includes an elongate member 112 having a proximal end 114, a distal end 116, and an inner passageway or lumen 118 extending therethrough between the proximal and distal ends 114, 116. The inner lumen 118 defines a fluid pathway. The elongate member 112 may optionally be formed as a portion of conduit 50a (FIG. 5) such that the pump 110 is in fluid communication with catheter 50 and downstream restriction device 20. As shown, the pump 110 can include multiple actuators 122a, 122b, 122c, 122d, 122e that are disposed around the outer surface 120 of the elongate member 112. In use, as will be explained in more detail below, the actuators 122a-122e can be sequentially activated using electrical energy to cause the actuators 122a-122e to radially contract, thereby contracting the elongate member 112 and forcing fluid to move in one direction therethrough. The actuators can also be configured to axially contract and expand to move fluid through the elongate member 112.

In an alternative embodiment, the expansion and contraction of actuators 122a-122e may be used only to increase or decrease internal pressure within the band without actually moving fluid. In this embodiment, the pump 110 could be disposed anywhere in fluid communication with the restriction system. Upon the application of energy to the one or more of the actuators 122a-122e, the volume of the inner lumen 118 would be changed, effecting a corresponding pressure change in the system 10.

The elongate member 112 can have a variety of configurations, but in one exemplary embodiment it is in the form of a flexible elongate tube or cannula that is configured to receive fluid flow therethrough, and that is configured to flex and/or change size in response to orientational changes in the actuators 122a-22e. The shape and size of the elongate member 112, as well as the materials used to form a flexible and/or elastic elongate member 112, can vary depending upon the intended use. In certain exemplary embodiments, the elongate member 112 can be formed from a biocompatible polymer, such as silicone or latex. Other suitable biocompatible elastomers include, by way of non-limiting example, synthetic polyisoprene, chloroprene, fluoroelastomer, nitrile, and fluorosilicone. A person skilled in the art will appreciate that the materials can be selected to obtain the desired mechanical properties. While not shown, the elongate member 112 can also include other features to facilitate attachment thereof to a medical device, a fluid source, etc.

The actuators 122a-122e can also have a variety of configurations. In the illustrated embodiment, the actuators 122a-122e are formed into an annular member from an EAP laminate or composite that is rolled around an outer surface 120 of the elongate member 112. An adhesive or other mating technique can be used to attach the actuators 122a-122e to the elongate member 112. The actuators 122a-122e are preferably spaced a distance apart from one another to allow the actuators 122a-122e to radially contract and axially expand when energy is delivered thereto, however they can be positioned in contact with one another. A person skilled in the art will appreciate that actuators 122a-122e can alternatively be disposed within the elongate member 112, or they can be integrally formed with the elongate member 112. The actuators 122a-122e can also be coupled to one another to form an elongate tubular member, thereby eliminating the need for the flexible member 112. A person skilled in the art will also appreciate that, while five actuators 122a-122e are shown, the pump 110 can include any number of actuators (e.g., ranging from two to more than five). For example, the number and position of the actuators can be varied to control the flow and/or pressure characteristics of the pump and the pumping action. The actuators 122a-122e can also have a variety of configurations, shapes, and sizes to alter the pumping action of the device.

As shown, the actuators 122a-122e can be coupled to the flexible elongate member 112 in a variety of orientations to achieve a desired fluid movement. In an exemplary embodiment, the orientation of the actuators 122a-122e is arranged such that the actuators 122a-122e will radially contract and axially expand upon the application of energy thereto. In particular, when energy is delivered to the actuators 122a-122e, the actuators 122a-122e can decrease in diameter, thereby decreasing an inner diameter of the elongate member 112. Such a configuration allows the actuators 122a-122e to be sequentially activated to pump fluid through the elongate member 112, as will be discussed in more detail below. A person skilled in the art will appreciate that various techniques can be used to deliver energy to the actuators 122a-122e. For example, each actuator 122a-122e can be coupled to a return electrode and a delivery electrode that is adapted to communicate energy from a power source to the actuator. The electrodes can extend through the inner lumen 18 of the elongate member 112, be embedded in the sidewalls of the elongate member 112, or they can extend along an external surface of the elongate member 112. The electrodes can couple to a battery or other energy source. Where the pump 110 is adapted to be implanted within the patient, the electrodes can be coupled to a transformer that is adapted to be subcutaneously implanted and that is adapted to store energy and/or receive energy from an external source located outside of the patient's body. An exemplary configuration is shown in FIG. 5, in which the transformer or power source is contained in the sensor housing 60 and sensor/power leads 101 deliver energy to the pump 110.

Alternatively, energy can be supplied by an external device (e.g., the reading device 70 shown in FIG. 1A) that can transcutaneously deliver energy to the sensor housing 60 (FIG. 5), e.g., when the external device is moved in proximity of the sensor housing 60. The external device can be mobile (e.g., a wand or hand-held unit that can be waved or otherwise placed in proximity of the sensor housing 60) or stationary (e.g., a bedside, desk-mounted, or car-mounted box that the patient can move near).

Figure 6C:
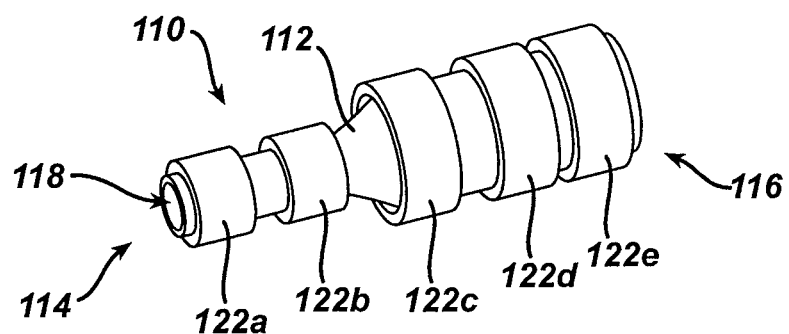
FIG. 6C is a perspective view of the pump of FIG. 6A with the first and second actuators activated.
Figure 6D:
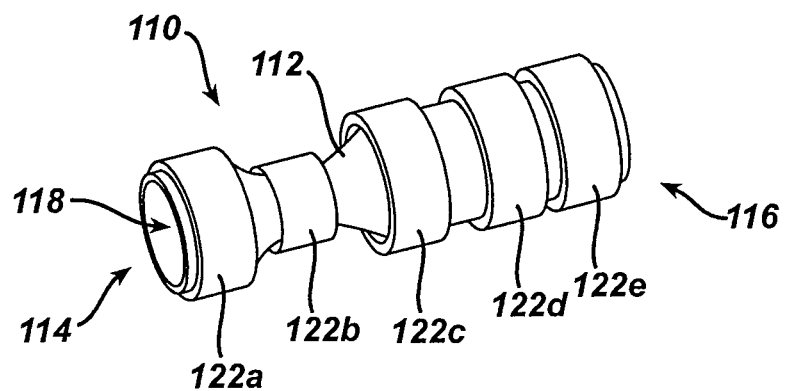
FIG. 6D is a perspective view of the pump of FIG. 6A with the first actuator deactivated and the second actuator activated.
Figure 6E:
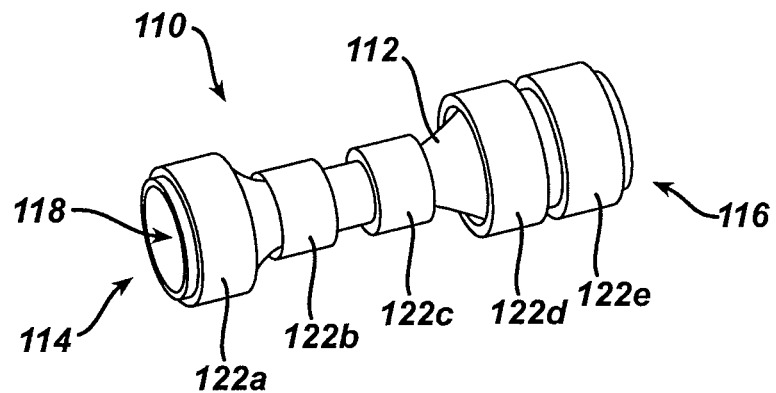
FIG. 6E is a perspective view of the pump of FIG. 6A with the second and third actuators activated.
Figure 6F:
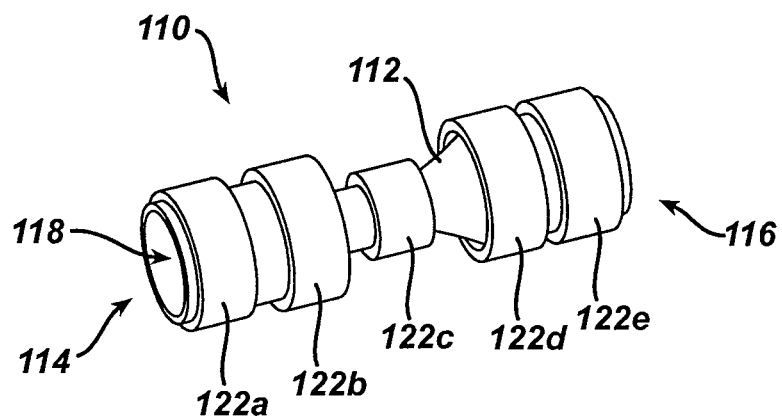
FIG. 6F is a perspective view of the pump of FIG. 6A with the second actuator deactivated and the third actuator activated.
Figure 6G:
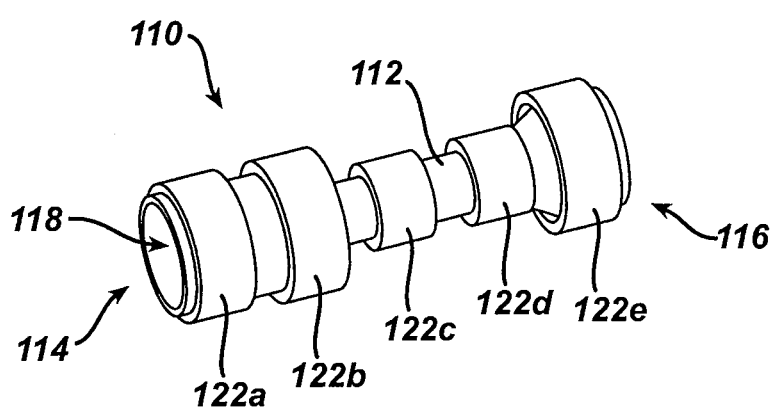
FIG. 6G is a perspective view of the pump of FIG. 6A with the third and fourth actuators activated.

FIGS. 6B-6G illustrate one exemplary method for sequentially activating the actuators 122a-122e to create a peristaltic-type pumping action. In this exemplary embodiment the pump moves fluid in a distal direction toward band FIG. 1B), which would be located distally of the pump 110. The sequence can begin by delivering energy to a first actuator 122a such that the actuator constricts a portion of the elongate member 112 and reduces the diameter of the inner lumen 118. While maintaining energy delivery to the first actuator 122a, energy is next delivered to a second actuator 122b adjacent to the first actuator 122a. The second actuator 122b radially contracts, i.e., decreases in diameter, to further compress the elongate member 112, as illustrated in FIG. 6C. As a result, fluid within the inner lumen 118 adjacent to actuators 122a and 122b will be forced in the distal direction toward the distal end 116 of the elongate member 112. As shown in FIG. 6D, while maintaining energy delivery to the second actuator 122b, energy delivery to the first actuator 122a can be terminated, thereby causing the first actuator 122a to radially expand and return to an original, deactivated configuration. Energy can then be delivered to a third actuator 122c adjacent to the second actuator 122b to cause the third actuator 122c to radially contract, as shown in FIG. 6E, further pushing fluid through the inner lumen 118 in a distal direction. Energy delivery to the second actuator 122b can then be terminated such that the second actuator 122b radially expands to return to its original, deactivated configuration, as shown in FIG. 6F. Energy can then be delivered to a fourth actuator 122d, as shown in FIG. 6G, to radially contract the fourth actuator 122d and further pump fluid in the distal direction. This process of sequentially activating and de-activating adjacent actuators is continued resulting in a "pulse" which travels from the proximal end 114 of the pump 110 to the distal end 116 of the pump 110. The process illustrated in FIGS. 6B-6G can be repeated, as necessary, to continue the pumping action. For example, energy can be again delivered to actuators 122a-122e to create a second pulse. One skilled in the art will appreciate that the second pulse can follow directly behind the first pulse by activating the first actuator 122a at the same time as the last actuator 122d, or alternatively the second pulse can follow the first pulse some time later. One skilled in the art will further appreciate that the sequence described above can be reversed to effect flow in a proximal direction, i.e., away from the band.

Figure 7:
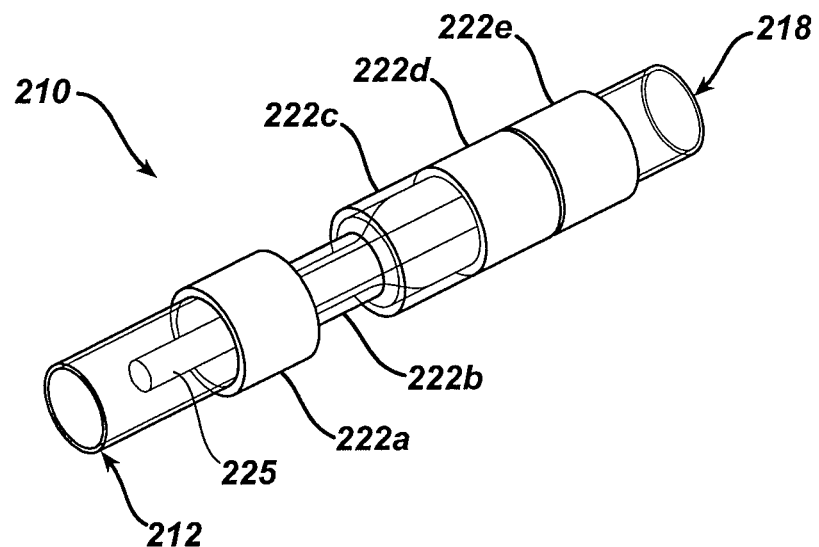
FIG. 7 is a perspective view of one exemplary embodiment of a pump having multiple actuators disposed around a flexible tube including a reaction surface.
Figure 8:
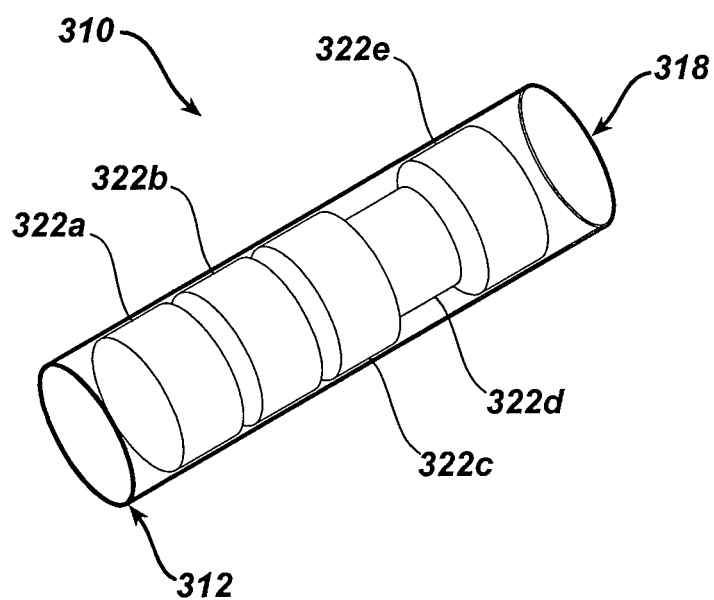
FIG. 8 is a perspective view of one exemplary embodiment of a pump having multiple actuators disposed within a tubular member.
Figure 9:
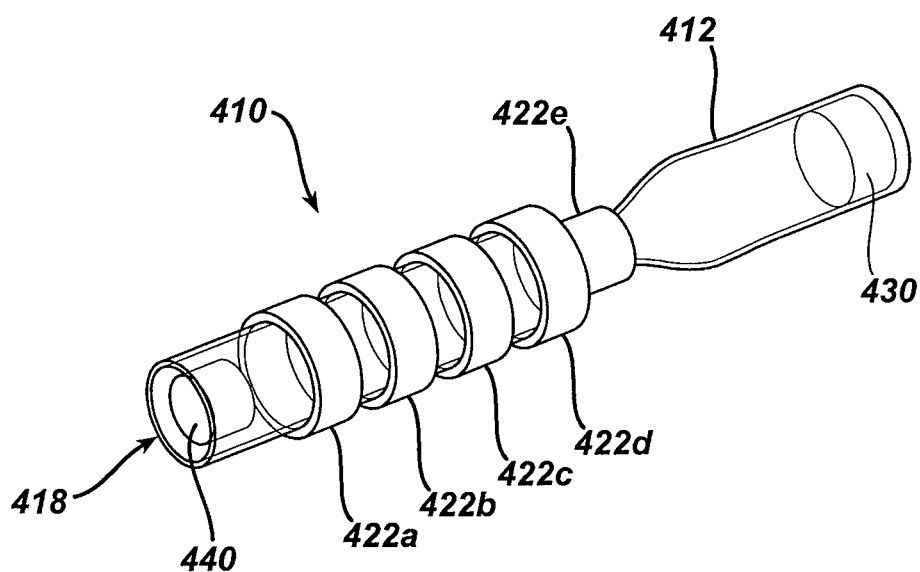
FIG. 9 is a perspective view of one exemplary embodiment of a pump having actuators disposed both around and within a flexible tubular member.

The pump 110 can also include one or more actuators configured to form a valve. By forming a valve using one or more of the actuators, the pressure and volume of fluid in the band 20 (FIG. 1B) can be maintained without the need for additional components. In one embodiment, not shown, at least one of the actuators 122a-122e is adapted to form a valve by constricting a portion of the elongate member 112 to an extent sufficient to prevent fluid flow through the inner lumen 118. In this embodiment the elongate member 112 is constricted by one or more of the actuators 122a-122e until the inner walls of the elongate member 112 are in contact (or close proximity) with each other, preventing fluid flow through the compressed segment and thus serving as a valve. FIGS. 7-9 show various other embodiments in which the actuators can form a valve.

In the embodiment shown in FIG. 7, the pump 210 includes a plurality of actuators 222a-222e, which are formed around elongate member 212, and a reaction surface 225, which can be formed from a non-compressible material, disposed within the elongate member 212. In a contracted state, actuators 222a-222e compress the elongate member 212 against the reaction surface 225, thereby sealing the inner lumen and forming a valve. Similar to the actuators discussed above with respect to FIGS. 6B-6G, the actuators 222a-222e are in a non-compressed state in their relaxed or natural configuration, thus allowing a portion of the lumen within the elongate member 212 to remain open. The actuators 222a-222e contract when energy is delivered thereto. Using the same method described above, the actuators can be sequentially activated to create a peristaltic-type pumping action. When energy is delivered to one or more of the actuators, e.g., actuator 222b as shown in FIG. 7, the actuator will compress the elongate member 212 against the reaction surface 225 thereby preventing fluid flow through the compressed segment and thus serving as a valve. One skilled in the art will appreciate that the actuators can alternatively be configured such that in their relaxed state the actuators are closed and compress the elongate member 212 against the reaction surface 225. Upon the delivery of energy to such actuators, the actuators will expand and allow fluid to pass through the affected segments of the lumen 218. One skilled in the art will further appreciate that the sequence of activating the actuators can be controlled to effect flow in a proximal direction, i.e., away from the band, or in a distal direction, i.e., towards the band.

In another embodiment, shown in FIG. 8, the pump 310 includes actuators 322a-322e that are disposed entirely within elongate member 312. In this embodiment, the actuators 322a-322e can be in the form of solid members that can be of a variety of shapes, including a disk-like shape as shown. Further, the actuators are configured to radially expand or contract when energy is delivered thereto. For example, as shown in FIG. 8, the actuators can be in an expanded form in their relaxed state. In such a relaxed state the actuators occlude the lumen 318 within the elongate member 312 and prevent passage of fluid through the affected segment of the lumen. However, when energy is applied, such as to actuator 322d in FIG. 8, the actuator compresses to allow fluid to flow between an outer surface of actuator 322d and an adjacent inner surface of elongate member 312. Thus, fluid can flow past the actuators 322a-322e in their contracted state, but the actuators 322a-322e form a valve that prevents fluid flow when they are in their expanded state. A peristaltic-type pumping action can also be created by sequentially activating and deactivating the actuators 322a-322e in the manner discussed above. One skilled in the art will also appreciate that the pump of FIG. 8 can be alternatively configured such that the actuators are in a compressed configuration when in their natural state, thus allowing fluid flow, and in an expanded configuration when energy is applied thereto. One skilled in the art will further appreciate that the sequence of activating the actuators can be controlled to effect flow in a proximal direction, i.e., away from the band, or in a distal direction, i.e., towards the band.

In yet another embodiment, shown in FIG. 9, the pump 410 can include both internal and external actuators. As shown, the pump 410 includes substantially solid actuators 430, 440 contained entirely inside the elongate member 412, and annular actuators 422a-422e formed on the outer surface of the elongate member 412. Any number of internal and external actuators 422a-422e, 430, 440 may be provided, and the actuators can be formed in any configuration. For example, the external actuators 422a-422e can be located between a pair of internal actuators 430, 440, which may form terminal ends of the pump. In this configuration, the internal actuators 430, 440 can operate as valves as described in detail above. For example, one of the internal actuators, e.g., actuator 430 as shown in FIG. 9, can be in an expanded form in its relaxed state to seal the inner lumen of the elongate member 412 at one terminal end of the pump. Using methods similar to those described above, the actuators can be sequentially activated to create a peristaltic-type pumping action. For example, in the configuration shown in FIG. 9, the external actuators 422a-422e can be sequentially activated and de-activated, as described above, resulting in a fluid "pulse" that travels through the inner lumen 418 of the elongate member 412. The sequential activation of the external actuators can be repeated, as necessary, to continue the pumping action. One skilled in the art will appreciate that other arrangements and configurations of internal and external actuators are possible. For example, an internal actuator 430, 440 may be located between each pair of external actuators 422a-422e. In addition, one skilled in the art will appreciate that the sequence of activating the actuators can be controlled to effect flow in a proximal direction, i.e., away from the band, or in a distal direction, i.e., towards the band.

One skilled in the art will appreciate that while the actuators are discussed in terms of an ability to contract and expand radially, they can alternatively be configured to contract and expand axially.

As discussed above, a fluid reservoir need not be present in the system. Instead, the elongate member 112, 212, 312, 412 shown in FIGS. 6A-9 could also serve as means for holding an additional supply of fluid. For example, the upstream (proximal) side of the elongate member 112, 212, 312, 412 can be oversized and filled with an additional volume of fluid to meet the operational needs of the system. Activation of one or more of the actuators, as discussed above, can cause fluid to move either toward or away from a band, which would be disposed distally of the pump. One skilled in the art will appreciate that, in the embodiment discussed above in which the expansion and contraction of actuators is used to increase or decrease internal pressure within the band without actually moving fluid, an additional volume of fluid is not needed to effect a pressure change in the system 10.

Additional information on EAP pump technology is also disclosed in commonly-owned U.S. Patent Application Publication No. 2007/0025868 A1, entitled "Electroactive Polymer-Based Pump," filed on Jul. 28, 2005, which is hereby incorporated by reference in its entirety.

The present invention also provides a method of adjusting pressure in an implantable restriction device system 10. In one embodiment, the method can include sensing a clinically relevant parameter and adjusting a pressure within the restriction device in response to the sensed clinically relevant parameter by activating a pump in fluid communication with the restriction device 20. The EAP-based pump can be the type described with respect to FIGS. 6A-9. That is, the pump can be formed of a plurality of actuators configured to change shape upon the application of energy thereto such that sequential activation of the plurality of actuators is effective to create pumping action to move fluid through the pump. The clinically relevant parameter can be sensed using an implantable sensor.

In one embodiment, the sensed clinically relevant parameter is a pressure, although it is understood that it can include any one of the other parameters identified above, as well as other clinically relevant parameters. In this embodiment, the pressure can be sensed using an implantable pressure sensor 62, as discussed above. The method can include sensing a pressure in an implanted restriction device 10a, comparing the sensed pressure to a desired pressure (including a desired pressure range), and adjusting the pressure within the restriction device 10a to be approximately equal to the desired pressure (or desired pressure range) if the sensed pressure is not equal to the desired pressure (or desired pressure range) by activating a pump in fluid communication with the restriction device 20 to achieve a desired pressure (or desired pressure range) in the restriction device.

In one embodiment, activation of the pump 110 could automatically occur if the sensed clinically relevant parameter (e.g., pressure, etc.) in the band 30 were higher than a desired value or range, in which case fluid could be pumped out of the band 30 to reduce the pressure. Conversely, if the sensed parameter in the band 30 were lower than a desired value or range, the fluid could be pumped into the band (e.g., from a reservoir or from an implanted catheter) until a desired target for the parameter is achieved. In yet another configuration, if a sensed clinically relevant parameter (e.g., absolute pressure at a given duration, pressure gradient, etc.) in the band 30 which correlates with undesirable eating habits was measured, the fluid could be pumped into the band (e.g., from a reservoir or from an implanted catheter) until a sufficient restriction was created. This restriction would provide feedback to the patient (which can be immediate or delayed) to stop eating by inducing a physiologic response (e.g., vomiting, etc.). The restriction would be sustained in place until a triggering event (e.g., elapsed time) occurred to return the system to a normal operating state. For safety purposes, an override which can be activated by the patient or other caregiver may be provided. This override may be activated through a function in the external portion 10b of the food intake restriction system 10. Other techniques for automatic actuation can be used such as timer control, or the system can be programmed to activate the pump in response to certain sensed parameters or events, or according to a programmed schedule. For example, the implantable pump can effect a pressure increase within the restriction device (i.e., move fluid towards the restriction device) when a patient is determined to be eating, or when the patient is awake (or during selected hours of a day) and effect a pressure decrease within the restriction device (i.e., move fluid away from the restriction device) when the patient is asleep (or during other selected hours of a day). Those skilled in the art will appreciate that the programmed schedule can be based on a multitude of factors including type of day (e.g., holidays, weekday, weekend), anticipated patient activities, and the like. Those skilled in the art will appreciate that the pressure in the band 30 can be controlled using closed-loop methods such as PID (proportional-integral-derivative) control schemes or other appropriate methods including digital control schemes.

One skilled in the art will appreciate that certain safety features may be built into the pump design to provide contingencies in the event of a malfunction or a loss of power. By way of example, if a power outage (or malfunction) is detected, or if the remaining power falls below a predetermined threshold, the system can be configured to default to a relaxed state in which the restriction is relaxed and/or opened until the power level is restored or the malfunction corrected.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used system is obtained and if necessary cleaned. The system can then be sterilized by any known and suitable technique, including ethylene oxide sterilization. In one sterilization technique, the system is placed in a closed and sealed container, such as a plastic or TYVEK bag. The container and system are then placed in a field of radiation that can penetrate the container, such as gamma radiation, x-rays, or high-energy electrons. The radiation kills bacteria on the system and in the container. The sterilized system can then be stored in the sterile container. The sealed container keeps the system sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A restriction system for forming a restriction in a patient, comprising:
    an implantable restriction device that is adjustable and configured to form a restriction in a patient; and
    an implantable pump in fluid communication with the restriction device and having a plurality of actuators configured to change shape upon the application of energy thereto such that sequential activation of the plurality of actuators is effective to create pumping action to move fluid through the pump, at least one of the actuators being configured to prevent the passage of fluid when in a relaxed state such that the at least one actuators is in expanded form.

2. The system of claim 1, further comprising an implantable port configured to receive fluid from a fluid source external to the patient wherein the implantable port is in fluid communication with the implantable restriction device and the pump.

3. The system of claim 1, further comprising an implantable sensor in communication with the restriction device.

4. The system of claim 3, wherein the implantable sensor is configured to measure at least a pressure within the restriction device.

5. The system of claim 1, wherein the pump further comprises a first member having a passageway formed therethrough and being in communication with the plurality of actuators.

6. The system of claim 5, wherein the actuators are disposed within the first member.

7. The system of claim 5, wherein the actuators are disposed outside the first member.

8. The system of claim 1, wherein at least one actuator is configured to expand upon the application of energy thereto.

9. The system of claim 1, wherein at least one actuator is configured to contract upon the application of energy thereto.

10. The system of claim 1, wherein the actuators are configured to move sequentially.

11. The system of claim 1, wherein each actuator comprises an electroactive polymer.

12. The system of claim 1, wherein fluid moves in a direction from the pump to the restriction device.

13. The system of claim 1, wherein fluid moves in a direction from the restriction device to the pump.

14. The system of claim 1, wherein the implantable pump effects a pressure change within the restriction device in accordance with at least one of a detected event and a programmed schedule.

15. The system of claim 1, further comprising a fluid reservoir in fluid communication with the pump.

16. The system of claim 15, wherein the fluid reservoir is configured to hold in the range of approximately 0.1 to 20 ml of fluid.

* * * * *